US010273469B2

(12) United States Patent
Dominguez Vera et al.

(10) Patent No.: US 10,273,469 B2
(45) Date of Patent: Apr. 30, 2019

(54) PROBIOTIC BACTERIA COMPRISING METALS, METAL NANOPARTICLES AND USES THEREOF

(71) Applicant: BIOSEARCH, S.A., Granada (ES)

(72) Inventors: Jose Manuel Dominguez Vera, Armilla-Granada (ES); Natividad Galvez Rodriguez, Cenes de la Vega-Granada (ES); Miguel Angel Martin Marcos, Armilla-Granada (ES); Fernando Carmona Rodriguez-Acosta, Granada (ES); Deyanira Rondon Rodriguez, Armilla-Granada (ES); Monica Olivares Martin, Huetor Vega-Granada (ES)

(73) Assignee: BIOSEARCH, S.A., Granada (ES)

( * ) Notice: Subject to any disclaimer, the term of this patent is extended or adjusted under 35 U.S.C. 154(b) by 75 days.

(21) Appl. No.: 14/901,304

(22) PCT Filed: Jun. 24, 2014

(86) PCT No.: PCT/EP2014/063246
§ 371 (c)(1),
(2) Date: Dec. 28, 2015

(87) PCT Pub. No.: WO2014/206969
PCT Pub. Date: Dec. 31, 2014

(65) Prior Publication Data
US 2016/0160207 A1 Jun. 9, 2016

(30) Foreign Application Priority Data
Jun. 25, 2013 (EP) .................... 13384202

(51) Int. Cl.
A61K 39/39 (2006.01)
A61K 39/00 (2006.01)
A61K 49/00 (2006.01)
C12N 11/14 (2006.01)
A61K 33/24 (2019.01)
A61K 35/744 (2015.01)
A61K 35/745 (2015.01)
A61K 35/747 (2015.01)
C12N 1/20 (2006.01)
A61K 49/18 (2006.01)
A61K 33/04 (2006.01)
A61K 33/06 (2006.01)
A61K 33/16 (2006.01)
A61K 33/18 (2006.01)
A61K 33/20 (2006.01)
A61K 33/26 (2006.01)
A61K 33/30 (2006.01)
A61K 33/32 (2006.01)
A61K 33/34 (2006.01)
A61K 9/00 (2006.01)
A23L 33/135 (2016.01)
A23L 33/16 (2016.01)
A23L 33/165 (2016.01)

(52) U.S. Cl.
CPC ............ C12N 11/14 (2013.01); A23L 33/135 (2016.08); A23L 33/16 (2016.08); A23L 33/165 (2016.08); A61K 9/0053 (2013.01); A61K 33/04 (2013.01); A61K 33/06 (2013.01); A61K 33/16 (2013.01); A61K 33/18 (2013.01); A61K 33/20 (2013.01); A61K 33/24 (2013.01); A61K 33/26 (2013.01); A61K 33/30 (2013.01); A61K 33/32 (2013.01); A61K 33/34 (2013.01); A61K 35/744 (2013.01); A61K 35/745 (2013.01); A61K 35/747 (2013.01); A61K 49/1896 (2013.01); C12N 1/20 (2013.01); A23V 2002/00 (2013.01)

(58) Field of Classification Search
CPC .... A61K 39/00; A61K 39/09; A61K 2201/00; A61K 2201/03; A61K 2201/034
USPC ......... 424/9.1, 9.2, 93.1, 93.4, 178.1, 234.1, 424/246.15
See application file for complete search history.

(56) References Cited

U.S. PATENT DOCUMENTS

| 7,280,863 | B2 | 10/2007 | Shachar |
|---|---|---|---|
| 2004/0019447 | A1 | 1/2004 | Shachar |
| 2005/0013759 | A1 | 1/2005 | Grow |
| 2006/0114088 | A1 | 6/2006 | Shachar |
| 2006/0116634 | A1 | 6/2006 | Shachar |

(Continued)

FOREIGN PATENT DOCUMENTS

| EP | 2283810 A1 | 2/2011 |
|---|---|---|
| WO | 0115714 A1 | 3/2001 |

(Continued)

OTHER PUBLICATIONS

International Preliminary Report on Patentability for International Application No. PCT/EP2014/063246. (27 pages). (dated Jan. 4, 2016).
Nair et al., "Coalescence of Nanoclusters and Formation of Submicron Crystallites Assisted by Lactobacillus Strains", Crystal Growth & Design, 2002, vol. 2, No. 4, pp. 293-298.
"Database WPI", Thomson Scientific, 2009, 2 pages.
International Search Report for International Application No. PCT/EP2014/063246. (dated Aug. 13, 2014) (4 pages).

(Continued)

Primary Examiner — Rodney P Swartz
(74) Attorney, Agent, or Firm — Lucas & Mercanti, LLP

(57) ABSTRACT

The invention relates to probiotic bacteria selected from lactic acid bacteria, such as *Lactobacillus* and Bifidobacteria, having metals and/or metal nanoparticles and to foodstuff and pharmaceutical composition having these bacteria. The invention also provides methods for obtaining these bacteria and uses of these bacteria for the treatment and prevention of mineral deficiency pathologies, as a contrast agent for the imaging of the digestive tract and for the treatment of cancer.

19 Claims, 8 Drawing Sheets

(56) References Cited

U.S. PATENT DOCUMENTS

| | | | |
|---|---|---|---|
| 2006/0129327 A1* | 6/2006 | Kim | B82Y 5/00 702/19 |
| 2007/0116006 A1 | 5/2007 | O'Rourke et al. | |
| 2008/0249395 A1 | 10/2008 | Shachar et al. | |
| 2009/0239280 A1 | 9/2009 | De Windt et al. | |
| 2010/0158952 A1* | 6/2010 | Goletz | A23L 33/135 424/243.1 |
| 2010/0272770 A1 | 10/2010 | De Windt et al. | |
| 2010/0278975 A1 | 11/2010 | Chung et al. | |

FOREIGN PATENT DOCUMENTS

| | | |
|---|---|---|
| WO | 2004003235 A2 | 1/2004 |
| WO | 2008145756 A1 | 12/2008 |
| WO | 2011056685 A1 | 5/2011 |
| WO | 2011061259 A1 | 5/2011 |

OTHER PUBLICATIONS

Massart, "Preparation of Aqueous Magnetic Liquids in Alkaline and Acidic Media" IEE Transactions on Magnetics, 1981, vol. Mag-17, No. 2, pp. 1247-1248.

Shaw et al., Determination of the Minimal Temperature for Growth of *Escherichia coli* , Journal of Bacteriology, 1971, vol. 105, No. 2, pp. 683-684.

Delgado et al., "Measurement and Interpretation of Electrokinetic Phenomena", Pure Appl. Chem., 2005, vol. 77, No. 10, pp. 1753-1805.

Overgaard, "Effect of Hyperthermia on Malignant Cells in Vivo", Cancer, 1977, vol. 39, pp. 2637-2646.

Liu et al., "Magnetically Sensitive Alginate-Templated Polyelectrolyte Multilayer Microcapsules for Controlled Release of Doxorubiein", J. Phys. Chem. C., 2010, vol. 114, pp. 7673-7679.

Hu et al., "Remotely nano-rupturable yolk/shell capsules for magnetically-triggered drug release", Chem. Commun., 2011, vol. 47, pp. 1776-1778.

Vayssieres et al., "Size Tailoring of Magnetite Particles Formed by Aqueous Precipitation: An Example of Thermodynamic Stability of Nanometric Oxide Particles", Journal of Colloid Interface Science, 2008, vol. 205, pp. 205-212.

Shabtai, "Adsorption of Rhodococcus Strain GIN-1 (NCIMB 40340) on Titanium Dioxide and Coal Fly Ash Particles", Applied and Environmental Microbiology, 1994, pp. 3079-3088.

Pagnout et al., "Role of electrostatic interactions in the toxicity of titanium dioxide nanoparticles toward *Escherichia coli*", Colloids and Surfaces B: Interfaces, 2012, vol. 92, pp. 315-321.

Kloepfer et al., "Quantum Dots as Strain- and Metabolism-Specific Microbiological Labels", Applied and Environmental Microbiology, 2003, vol. 69, No. 7, pp. 4205-4213.

Huang et al., "Amine-Functionalized Magnetic Nanoparticles for Rapid Capture and Removal of Bacterial Pathogens", Environ. Sci. Technol., 2010, vol. 44, pp. 7908-7913.

Radovic-Moreno et al., "Surface Charge-Switching Polymeric Nanoparticles for Bacterial Cell Wall-Targeted Delivery of Antibiotics", ASC Nano, vol. 6, No. 5 pp. 4279-4287.

Hill et al., "Magnetic Resonance Imaging of Tumors Colonized with Bacterial Ferritin-Expressing *Escherichia coli*", PLOS ONE, 2011, vol. 6, Issue 10, 9 pages.

Cronin et al., "High Resolution in Vivo Bioluminescent Imaging for the Study of Bacterial Tumour Targeting", PLOS ONE, 2012, vol. 7, Issue 1, 11 pages.

* cited by examiner c)

PROBIOTIC BACTERIA COMPRISING METALS, METAL NANOPARTICLES AND USES THEREOF

CROSS REFERENCE TO RELATED APPLICATION

This Application is a 371 of PCT/EP2014/063246 filed on Jun. 24, 2014 which, in turn, claimed the priority of European Patent Application No. 13384202.1 filed on Jun. 25, 2013, both applications are incorporated herein by reference.

FIELD OF THE INVENTION

The present invention falls within the field of probiotic bacteria and, more specifically, it related to probiotic bacteria loaded with metallic ions and/or metal nanoparticles, to the use of these probiotic bacteria for the prophylaxis or treatment of mineral deficiency diseases, to the use of these bacteria as contrast agent for imaging of the digestive tract and to the use of these bacteria for the treatment of cancer.

BACKGROUND OF THE INVENTION

Minerals are one of the five fundamental groups of nutrients needed to life. Micronutrient malnutrition affects >50% of the worldwide population. In particular, iron, zinc and calcium are considered an emerging public health problem in most of developing countries. In developed countries there are also serious problems of deficiency of minerals due to improper eating habits that has prevailed the comfort and pleasure to health. Iron deficiency is the most common nutritional problem in the world. As well as affecting a large number of children and women in developing countries, it is the only nutrient deficiency which is also significantly prevalent in industrialized countries. The consequences of iron deficiency anemia are very serious. Anemia resulting from iron deficiency in young children has become very common since the level of bioavailable iron in a typical infant's diet is low while their rapid growth requires a much higher level of iron. The consequences of iron deficiency anemia (IDA) are very serious as it is associated with impaired cognitive and psychomotor development, reduced growth and decreased resistance to infection.

To increase the daily intake of these minerals, numerous food supplements containing different inorganic and organic forms of these metals are commercially available. At any rate, it is quite well known that inorganic salts have a very low bioavailability. Organic salts, commonly based on gluconate, citrate, or other molecules, are characterized by a higher systemic effect. Therapeutic doses of iron supplements, which are prescribed for iron deficiency anemia, may cause gastrointestinal side effects such as nausea, vomiting, constipation, diarrhea, dark colored stools, and/or abdominal distress. Therefore, there is a need of providing new formulations for metal supplementation, in particular for iron supplementation, with minimum gastrointestinal side effects.

SUMMARY OF THE INVENTION

In a first aspect, the invention relates to a bacterium selected from a lactic acid bacterium and a bacterium of the genus *Bifidobacterium* comprising at least one metal nanoparticle bound to its surface.

In second aspect, the invention relates to a method for obtaining a bacterium selected from a lactic acid bacterium and a bacterium of the genus *Bifidobacterium* comprising at least one metal bound to its surface, comprising contacting said bacterium with at least said metal, wherein said contacting is carried out in the presence of at least one salt of a divalent cation and at a temperature wherein the growth of said bacterium is substantially reduced.

In a third aspect, the invention relates to a bacterium obtainable by the method according to the second aspect.

In a fourth aspect, the invention relates to a biologically pure culture of a bacterium according to the first aspect or a bacterium according to the third aspect.

In a fifth aspect, the invention related to a foodstuff comprising a bacterium according to any the first aspect or a bacterium according to the third aspect or a biologically pure culture according to the fourth aspect.

In a sixth aspect, the invention relates to a pharmaceutical composition comprising a bacterium according to any the first aspect or a bacterium according to the third aspect or a biologically pure culture according to the fourth aspect and a pharmaceutically acceptable carrier.

In a seventh aspect, the invention relates to a bacterium selected from the bacterium of the first aspect and the bacterium of the third aspect, or a biologically pure culture according to the fourth aspect, for its use in the treatment and/or prevention of a disease or condition associated with a metal deficiency, wherein the bacterium comprises the metal that is deficient in said disease or condition and wherein the bacterium or culture is administered orally.

In an eighth aspect, the invention relates to a bacterium selected from the bacterium of the first aspect and the bacterium of the third aspect, or a biologically pure culture according to the fourth aspect, for its use in the treatment of cancer, wherein the metal is comprised in a magnetic nanoparticle.

In a ninth aspect, the invention relates to a non-therapeutic method for the delivery of a metal in the intestine of a subject, comprising the oral administration of a bacterium according to the first aspect or the bacterium of the third aspect or the biologically pure culture of the fourth aspect.

In a tenth aspect, the invention relates to the use of a bacterium according to any the first aspect or a bacterium according to the third aspect or a biologically pure culture according to the fourth aspect as contrast agent for magnetic resonance imaging, wherein the metal is comprised in a magnetic nanoparticle.

In an eleventh aspect, the invention relates to a method for the magnetic resonance imaging of the digestive tract of a subject which comprises:
  (i) orally administering to said subject a bacterium according to the first aspect, or a bacterium according to the third aspect, or a biologically pure culture according to the fourth aspect, or a contrast agent comprising a bacterium according to the first aspect, or a bacterium according to the third aspect, or a biologically pure culture according to the fourth aspect, wherein the metal is comprised in a nanoparticle and,
  (ii) detecting the metal nanoparticles in the digestive tract of the subject.

DETAILED DESCRIPTION OF THE INVENTION

Figure 1:
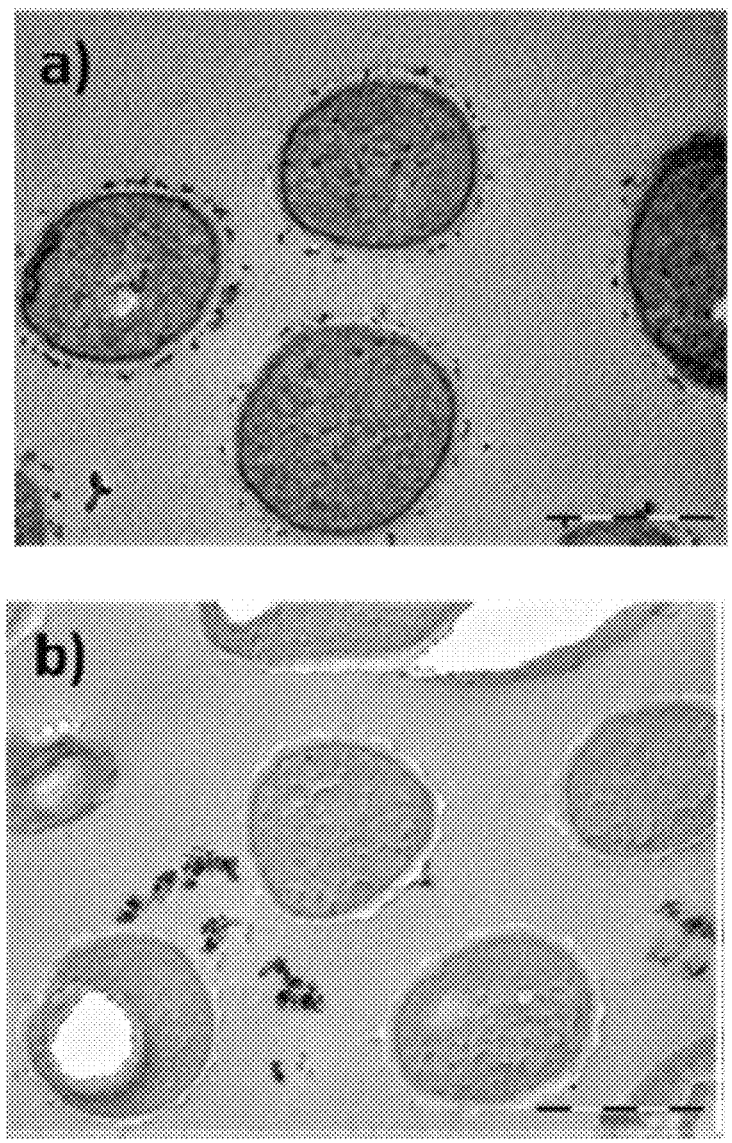
FIG. 1. Transmission Electron Microscopy images of fine-tuning layers of artificial magnetic bacterial embedded in an amorphous epoxy resin. a) positive and b) negative maghemite nanoparticles and c) bacteria without EPS biofilm. Note how grafting of nanoparticles takes place when bacteria contain EPS biofilm and the nanoparticles are positive. d) Fe mapping of a maghemite-containing bacteria showing as the iron selectively accumulates at the external bacteria surface.
Figure 1:
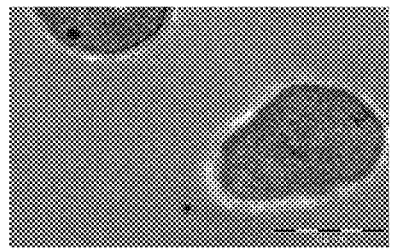
Figure 1:
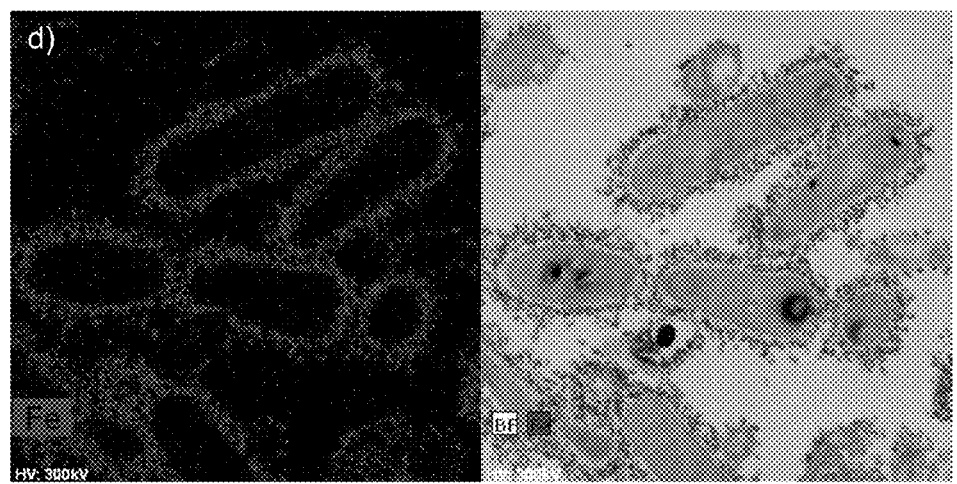

The inventors of the present invention have observed that a lactic acid bacterium or a bacterium of the genus *Bifidobacterium* is capable to bind a metal nanoparticle to its surface in a pH dependent manner. The association between the bacterium and the metal nanoparticle is stable under those pH conditions at which the nanoparticle has a positive surface charge (FIG. 1). Moreover, the inventors have observed that the pH conditions at which the metal nanoparticle is stably associated with the bacterium overlap with the acidic pH conditions in the stomach, whereas the pH conditions in the intestine allow the dissociation between the metal nanoparticle and the bacterium with the subsequent delivery of the metal nanoparticle (Example 2). Based on this property, the inventors have developed a method for administering metal supplements to subjects in need thereof by the oral administration of a bacterium containing metals and/or metal nanoparticles according to the invention. These bacteria, as well as a culture of these bacteria, can also be formulated as a pharmaceutical composition or form part of a foodstuff or nutricional product. Moreover, based on the ability of the lactic acid bacteria and bifidobacteria to reach tumor hypoxic areas, the nanoparticle-associated bacteria could also be used to target a compound of interest to a tumor. Further, the bacteria carrying magnetic nanoparticles associated to their surfaces are capable of destroying tumor cells when subjected to a selectively increase of the temperature (hyperthermia) in the vicinity of the tumor when applying an alternating magnetic field in the range of radiofrequency.

Finally, the present inventors have also seen that the metal-nanoparticle loaded bacteria are suitable for imaging the gastrointestinal system by magnetic resonance (MRI) (example 4). Thus these bacteria are also suitable for use as oral MRI contrast agents.

Bacterium and Culture

In a first aspect, the invention relates to a bacterium, hereinafter "bacterium of the invention", selected from a lactic acid bacterium and a bacterium of the genus *Bifidobacterium* comprising at least one metal nanoparticle bound to its surface.

The bacterium of the invention is selected from a lactic acid bacterium and a bacterium of the genus *Bifidobacterium*.

The term "lactic acid bacterium" or "LAB", as used herein, refers to any bacterium capable of producing, as the major metabolic end product of carbohydrate fermentation, lactic acid or at least one of its derivatives (including, but not limited to, acetic acid or propionic acid): the term is therefore intended to include propionic acid bacteria (PAB), which produce propionic acid as a carbohydrate fermentation product. Illustrative non-limitative examples of lactic acid bacteria are bacteria of the genera *Lactobacillus, Leuconostoc, Pediococcus, Lactococcus, Propionibacterium* and *Streptococcus* as well as the genera of the order *Lactobacillales Aerococcus, Carnobacterium, Enterococcus, Oenococcus, Teragenococcus, Vagococcus* and *Weisella*. Typically, the lactic acid bacterium is selected from the species *Leuconostoc* spp., *Lactococcus cremoris, Lactococcus lactis, Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbreuckii, Lactobacillus plantarum, Lactobacillus paraplantarum, Lactobacillus crispatus, Lactobacillus gasseri, Lactobacillus johnsonii* and *Lactobacillus jensenii*.

In a preferred embodiment, the lactic acid bacterium is a bacterium of the genus *Lactobacillus*. The term "*Lactobacillus*", as used herein, refers to a genus which is described in the NCBI database by the Taxonomy ID 1578. In a particular embodiment, the lactic acid bacterium is selected from the group consisting of *Lactobacillus fermemtum, Lactobacillus gasseri, Lactobacillus reuteri, Lactobacillus coryniformis, Lactobacillus casei, Lactobacillus paracasei, Lactobacillus plantarum, Lactobacillus salivarius* and *Lactobacillus bulgaricus*. In a more preferred embodiment, the lactic acid bacterium is *Lactobacillus fermentum*. The term "*Lactobacillus fermentum*" or "*L. fermentum*" refers to a species of the genus *Lactobacillus* which is described in the NCBI database by the Taxonomy ID 1613.

The term "bacterium of the genus *Bifidobacterium*" or "*bifidobacterium*", as used herein, refers to a genus of bacteria which is described in the NCBI database with the Tanoxonomy ID 1678. Illustrative non-limitative examples of suitable Bifidobacteria are the species *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis*, and *Bifidobacterium angulatum*. In a particular embodiment, the bacterium of the genus *Bifidobacterium* is selected from the group consisting of *Bifidobacterium breve*, *Bifidobacterium longum*, *Bifidobacterium infantum* and *Bifidobacterium animalis*. In a more preferred embodiment, the bacterium of the genus *Bifidobacterium* is *Bifidobacterium breve*. The term "*Bifidobacterium breve*" or "*B. breve*" refers to a species of the genus *Bifidobacterium* which is described in the NCBI database by the Taxonomy ID 1685.

In another particular embodiment, the lactic acid bacterium or the *bifidobacterium* of the invention is a bacterium which is capable of being transferred to the mammary gland after oral intake. For detecting the ability to being transferred to the mammary gland, an assay such as described in WO2004003235 for detecting transfer of a microorganism to the milk after oral intake can be used. Examples of such bacteria are disclosed in the international application WO2008145756. In a more particular embodiment, the lactic acid bacterium or the bacterium of the genus *Bifidobacterium* capable of being transferred to the mammary gland after oral intake is selected from the group consisting of:

*Bifidobacterium breve* deposited in the CECT under Accession No. 7263
*Lactobacillus fermentum* deposited in the CECT under Accession No. 5716
*Lactobacillus coryniformis* deposited in the CECT under Accession No. 5711
*Lactobacillus salivarius* deposited in the CECT under Accession No. 5713
*Lactobacillus gasseri* deposited in the CECT under Accession No. 5714
*Bifidobacterium breve* deposited in the CECT under Accession No. 7264
*Lactobacillus reuteri* deposited in the CECT under Accession No. 7260,
*Lactobacillus plantarum* deposited in the CECT under Accession No. 7262,
*Lactobacillus fermentum* deposited in the CECT under Accession No. 7265,
*Lactobacillus reuteri* deposited in the CECT under Accession No 7266,
*Enterococcus hirae* deposited in the CECT under Accession No 7410,
*Lactobacillus plantarum* deposited in the CECT under Accession No 7412,
*Enterococcus faecalis* deposited in the CECT under Accession No 7411,
*Lactobacillus salivarius* deposited in the CECT under Accession No 7409 and
*Lactobacillus reuteri* deposited in the CECT under Accession No 7413, The bacterium of the invention comprises at least one metal nanoparticle bound to its surface. The term "metal nanoparticle" as used herein, refers to a nanoparticle that comprises a metal. The term "nanoparticle" as used herein, refers to a particle having a diameter ranging from about 1 to about 1000 nanometers. In a particular embodiment, the nanoparticles for use according to the invention typically have an average particle diameter ranging from 2 to 50 nm, preferably from 4 to 10 nm, more preferably 8 nm. The average particle diameter is the average maximum particle dimension, it being understood that the particles are not necessarily spherical. The particle size may conveniently be measured using conventional techniques such as microscopy techniques, for example transmission electron microscopy. In one embodiment, the nanoparticles for use according to the invention have a spherical or substantially spherical shape. The shape may conveniently be assessed by conventional light or electron microscopy techniques.

The term "metal", as used herein, refers to any element, compound or alloy that is a good conductor of both electricity and heat. In a particular embodiment, the metal is selected from the group consisting of iron, manganese, cobalt, nickel, calcium, zinc, magnesium, potassium, copper, chromium, selenium, silicon, iodine and combinations thereof. In a preferred embodiment, the metal is selected from the group consisting of iron, calcium, zinc, selenium and a combination thereof. In a more preferred embodiment, the metal is iron.

In a particular embodiment, when the metal is selenium it is not in the form of selenocysteine.

The metal could be in a zero-oxidation-state or in the form of an oxide. In a more particular embodiment, the metal is in the form of an oxide. The term "metal oxide", as used herein, refers to any oxide of a metal element. The term "oxide" refers to any chemical compound containing one or several oxygen atoms in a −2 oxidation state, together with other elements. In a particular embodiment, the metal oxide is an iron oxide. Illustrative non-limitative examples of iron oxides that can form part of the nanoparticle of the bacterium of the invention are maghemite, magnetite, hematite, goethite and ferrihydrite. In a particular embodiment, the iron oxide is selected from the group consisting of maghemite, magnetite, hematite, goethite and ferrihydrite.

In an even more preferred embodiment, the iron oxide is maghemite.

The term "maghemite", as used herein, refers to an iron oxide mineral defined by the formula $\gamma\text{-}Fe_2O_3$.

The term "magnetite", as used herein, refers to an iron oxide mineral defined by the formula $Fe_3O_4$.

The term "hematite", as used herein, refers to an iron oxide mineral defined by the formula $\alpha\text{-}Fe_2O_3$.

The term "goethite", as used herein, refers to an iron oxide mineral defined by the formula $\alpha\text{-}FeO(OH)$.

The term "ferrihydrite", as used herein, refers to an iron oxide mineral defined by the formula $(Fe^{3+})_2O_3 \cdot 0.5H_2O$ or by the formula $[Fe^{3+}_{10}O_{14}(OH)_2]$.

In a particular embodiment of the bacterium of the invention, the nanoparticle is a magnetic nanoparticle. The term "magnetic nanoparticle", as used herein, refers to any nanoparticle with ferromagnetic and/or superparamagnetic behaviour. Non-limiting suitable examples can include, $Fe_2O_3$, $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZaFe_xO_y$, and $CdFe_xO_y$, wherein x and y vary between 1 and 6, depending on the method of synthesis known in the art. In a preferred embodiment, the magnetic nanoparticle comprises iron oxide. In a more preferred embodiment, the magnetic nanoparticle comprises maghemite.

The nanoparticles that can be attached to the bacteria according to the first aspect of the invention can be obtained by methods known by the person skilled in the art like, for example, the method described by Massart (Massart, R. IEEE Trans. Magn. 1981, 1247-1248) as illustrated in example 1.

In a preferred embodiment, the nanoparticles are directly bound to the bacteria, i.e. they do not contain any chemical group facing outwards or any coating which may form interactions with the components of the bacterial wall. In a preferred embodiment, the nanoparticles are not functionalized with amine groups. In another preferred embodiment, the metal nanoparticles are not coated with a polymeric component. In a still more preferred embodiment, the nanoparticles are not coated with a poly(D,L-lactic-co-glycolic acid)-b-poly(L-histidine)-b-poly-(ethylene glycol) (PLGA-PLH-PEG).

In a particular embodiment, the bacterium comprises a metal nanoparticle and at least one additional metal, for example, 2, 3, 4 or more additional metals. In this particular embodiment, said additional metal is different from the metal which forms the metal nanoparticle. In a more particular embodiment, the additional metal is selected from the group consisting of iron, manganese, cobalt, nickel, calcium, zinc, magnesium, potassium, copper, chromium, selenium, silicon, iodine and combinations thereof. In a preferred embodiment, the bacterium comprises a metal nanoparticle comprising iron, preferably iron oxide, more preferably maghemite, and one or more additional metals selected from the group consisting of manganese, cobalt, nickel, calcium, zinc, magnesium, potassium, copper, chromium, selenium, silicon, iodine and combinations thereof. In a more particular embodiment, the bacterium comprises a metal nanoparticle comprising iron, preferably iron oxide, more preferably maghemite, and one or more additional metals selected from the group consisting of calcium, zinc, selenium and a combination thereof. In a more particular embodiment, the bacterium comprises a metal nanoparticle comprising iron, preferably an iron oxide, more preferably maghemite, and further comprises a metal selected from zinc and calcium, more preferably it comprises zinc and calcium.

In a second aspect, the invention relates to a biologically pure culture of the bacterium of the first aspect of the invention.

The term "biologically pure culture", as used herein, refers to a culture in which the bacteria of the invention is found in a ratio of 95% or over, for example 96% or over, 97% or over, 98% or over, 99% or over or 100%, compared to other organisms present in the culture. The term "culture", as used herein, refers to a population of the bacteria of the invention. A culture may comprise other elements than the bacteria of the invention, such as the culture medium or any other substance that could be added to the culture medium beneficial for the culture growth or maintenance. The term "culture medium" or "medium" is recognized in the art, and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase that cells growing on a petri dish or other solid or semisolid support are exposed to. The term "medium" also refers to material that is intended for use in a cell culture, even if it has not yet been contacted with cells. In other words, a nutrient rich liquid prepared for bacterial culture is a medium. Similarly, a powder mixture that when mixed with water or other liquid becomes suitable for cell culture may be termed a "powdered medium". "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. Any conventional culture medium appropriate for lactic acid bacteria or bifidobacteria culture known in the art can be used in the present invention, such as, for instance, MRS medium, HANK'S medium, APT medium, RCM medium, LM17 medium, GM17 medium and Elliker medium. In a particular embodiment, the culture medium than can form part of the biologically pure culture of the invention is MRS medium. A description of MRS medium and other media appropriate for the culture of lactic acid bacteria and bifidobacteria can be found in Handbook of Culture Media for Food Microbiology, Vol. 34, edited by Janet. E. L. Cony, G. D. W. Curtis, Rosamund M. Baird.

Method for Obtaining the Bacterium

In a third aspect, the invention relates to a method for obtaining a bacterium selected from a lactic acid bacterium and a bacterium of the genus *Bifidobacterium* comprising at least one metal bound to its surface, comprising contacting said bacterium with at least said metal, wherein said contacting is carried out in the presence of at least one salt of a divalent cation and at a temperature wherein the growth of said bacterium is substantially reduced.

The terms "lactic acid bacterium", "bacterium of the genus *Bifidobacterium*", and "metal" have been previously described in connection with the first aspect of the invention.

According to the method of the third aspect, the contact between the acid lactic bacterium or the bacterium of the genus *Bifidobacterium* and the metal should be carried out in the presence of at least one salt of a divalent cation. The term "salt of a divalent cation", as used herein, refers to a compound in which a divalent cation is coupled to a counterion or is in solution. The term "divalent cation", as used herein, refers to an element in a positive oxidation state, resulting in a positive electrical charge with a valence of 2. Examples of divalent cations are $Fe^{2+}$, $Mn^{2+}$, $Co^{2+}$, $Ni^{2+}$, $Ca^{2+}$, $Zn^{2+}$, $Mg^{2+}$, $Cr^{2+}$, $Se^{2+}$ and $Si^{2+}$. Preferably, the salt of a divalent cation is selected from a salt of calcium, a salt of magnesium and a combination thereof. More preferably, the salt of a divalent cation is selected from calcium chloride, magnesium chloride and a combination thereof. Even more preferable, the salt of a divalent cation is a combination of calcium chloride and magnesium chloride. Without wanting to be bound to any particular theory, it is believed that the addition of the salt is able to affect the bacterium surface increasing its porosity and thereby increasing the metal binding.

According to the method of the third aspect, the contact between the acid lactic bacterium or the *bifidobacterium* and the metal should be carried out under temperature conditions wherein the growth of said bacterium is substantially reduced. The term "minimum growth temperature", as used herein, refers to the temperature below which sustained, balanced bacterial growth does not occur. The growth temperature suitable for carrying out the method according to the invention varies depending on the bacteria and should be determined for each species and strain of bacteria. The person skilled in the art knows methods and techniques for determining the temperature conditions wherein the growth of a bacterium is substantially reduced, such as the methods described by Shaw et al (Shaw et al, Journal of Bacteriology, 1971, Vol. 105 (2): 683-684). In a particular embodiment, the contact between the lactic acid bacterium or *bifidobacterium* and the metal is carried out at a temperature comprised between 0° C. and 10° C., more preferably at 0° C.

In a preferred embodiment, the temperature at which the contacting with the metal is carried out is a temperature at which the growth of the bacterium is reduced at least 50%, at least 60%, at least 70%, at least 80%, at least 90%, or more with respect to the growth of the bacteria at its optimum growth temperature.

In a particular embodiment, the lactic acid bacteria or the bifidobacteria are cooled to a temperature below the minimum growth temperature, for example 0° C., prior to the incubation with the metal, for example by storing the lactic acid bacterium or the *bifidobacterium* culture on ice for a time period of, for example, 10 minutes.

The lactic acid bacteria or the bifidobacteria that are going to be modified by the metal according to the method of the third aspect can be obtained by culture of the appropriate bacteria in standard culture conditions that are known by the person skilled in the art. In a particular embodiment, the lactic acid bacteria or the bifidobacteria derived from a 24 hour culture in MRS medium. In a preferred embodiment, the bacterium that is going to be treated with the method of the third aspect in order to obtain a bacterium that comprises a metal bound to its surface has been grown in a culture medium that do not comprises said metal. Without wanting to be bound to any particular theory, it is believed that since the bacterium is contacted with the metal under conditions that do not allow substantial bacterial growth, the metal does not significantly enter into the bacterium but it is incorporated on the bacterium surface.

In a particular embodiment of the method of the third aspect, the lactic acid bacterium or the *bifidobacterium* is contacted with a metal which is comprised in a nanoparticle. The term "nanoparticle" has been previously defined. In this particular embodiment, said contacting should be carried out at a pH in which the metal nanoparticle has a positive surface electrostatic charge. The term "surface electrostatic charge", as used herein, refers to the electrostatic charge or the particle that can be measured by the zeta potential of the nanoparticle. The term "zeta potential" refers to the electric potential in the interfacial double layer (DL) at the location of the slipping plane versus a point in the bulk fluid away from the interface. In other words, zeta potential is the potential difference between the dispersion medium and the stationary layer of fluid attached to the dispersed particle. The person skilled in the art knows how to calculate the zeta potential of a nanoparticle based on an experimentally-determined electrophoretic mobility or dynamic electrophoretic mobility (Delgado A V et al, 2005, Pure Appl. Chem. 77 (10): 1753-1850; Dukhin A S and Goetz P J "Ultrasound for characterizing colloids", Elsevier, 2002).

The pH at which the surface electrostatic charge of the metal nanoparticle is positive will depend on the nanoparticle composition, and can be determined by the person skilled in the art. For instance, when the metal nanoparticle comprises maghemite, the pH should be lower than: 5 In a preferred embodiment, when the metal nanoparticle comprises maghemite, the lactic acid bacterium or the *bifidobacterium* and the maghemite nanoparticle are incubated at a pH of 2.

These experimental conditions preserve the biofilm EPS (extracellular polymeric substance) of the bacteria. The presence of the EPS seems to be needed to graft the metal nanoparticles to the bacteria (FIG. 1c). In fact, when EPS biofilm is removed following standard protocols (Molecular cloning: a laboratory manual. Vol. 2. John J. Sambrook, David David, William Russell CSHL Press, 2001), the positive metal nanoparticles are not fixed to the external bacteria surface (FIG. 1c).

In a particular embodiment, a drying step is carried out before the incubation of the lactic acid bacterium or the *bifidobacterium* culture with the metal. Said drying step can be performed by any suitable technique known by the skilled person, such as centrifugation of the cell culture and decantation of the medium.

In a particular embodiment of the method of the third aspect, the lactic acid bacterium or the *bifidobacterium* is contacted with two or more metals. In a more particular embodiment, the bacterium is contacted with a first metal comprised in a nanoparticle, said contacting being carried out at a pH in which the nanoparticle has a positive electrostatic charge, and at least one additional metal different from the metal which is comprised in the nanoparticle. In an even more particular embodiment, the bacterium is contacted with an iron nanoparticle, for example a maghemite nanoparticle, and an additional metal selected from calcium, zinc, selenium and a combination thereof, preferably an additional metal selected from calcium, zinc and a combination thereof, more preferably a combination of calcium and zinc.

The metals can be provided by a solution comprising a compound comprising said metal, for example, a salt of said metal, or by a solution comprising nanoparticles comprising said metal.

When a bacterium comprising more than one additional metal is desired, the lactic acid bacterium or the *bifidobacterium* could be contacted with these additional metals in the same step, i.e. incubating the bacteria with a solution comprising the different additional metals or, preferably, the contact between the lactic acid bacterium or the *bifidobacterium* and each of the different metals can be perform in different successive incubation steps. In a particular embodiment, the additional step(s) is(are) carried out prior to the incubation of the lactic acid bacterium or the *bifidobacterium* with the metal nanoparticle. In a more particular embodiment, each additional step of contacting the bacterium with an additional metal is followed by a drying step. Said drying step can comprise, for example, centrifuging the mixture of the bacteria and the metal containing solution and removing the solution.

In a particular embodiment, the method of the third aspect comprises the steps of:

Contacting a lactic acid bacterium or a *bifidobacterium* with a first metal, for example, calcium.

Contacting the lactic acid bacterium or a *bifidobacterium* with a second metal, for example zinc.

Contacting the lactic acid bacterium or a *bifidobacterium* with a nanoparticle comprising a third metal, for example iron, preferably maghemite.

In further aspects, the invention is also related with a bacterium obtainable by the method of the third aspect, with a bacterium obtained by the method or the third aspect and with the biologically pure culture thereof. The term "biologically pure culture" has been previously defined.

Foodstuff and Pharmaceutical Compositions

The bacterium of the first aspect and the bacterium obtainable by the method of the third aspect can be orally administered to a subject both in the form of a foodstuff or in the form of a pharmaceutical composition.

Thus, in another aspect, the invention relates to a foodstuff comprising a bacterium according to the first aspect or a bacterium obtainable by the method of the third aspect or a biologically pure culture thereof.

The term "foodstuff", as used herein, refers to a substance or composition which is suitable for human and/or animal consumption. The foodstuff according to the present invention may relate to a foodstuff in a form which is ready for consumption. Alternatively or in addition, however, the term foodstuff as used herein may mean one or more food materials which are used in the preparation of a foodstuff. Non-limiting examples of suitable foodstuffs which can be used in the present invention are milk, yoghourt, cheese, curd, fermented milks, milk based fermented products, fermented cereal based products, fermented meat products, other milk based or cereal based powders, clinical nutrition formula, ice-creams, juices, bread, cakes or candies, animal feed formulations, semi- or synthetic diet formulations, infant formulae, clinical nutrition formulae, ice-creams, juices, flours, bread, cakes, candies or chewing-gums. The person skilled in the art knows how to prepare foodstuff from probiotic bacteria, like for example, the bacteria of the invention.

In another aspect, the invention relates to a pharmaceutical composition comprising a bacterium according to the first aspect or a bacterium obtainable by the method of the third aspect or a biologically pure culture thereof and a pharmaceutically active excipient.

The term "pharmaceutical composition", as used herein, refers to a composition intended for use in therapy. The pharmaceutical composition is directed to the oral administration and can take the form of tablets, capsules, liquid bacterial suspensions, dried oral supplements, wet oral supplements, dry tube feeding or a wet tube feeding.

The term "pharmaceutically acceptable carrier", as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, solutol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations such as DMSO (dimethylsulphoxide) and its derivatives. Remington's Pharmaceutical Sciences. Ed. by Gennaro, Mack Publishing, Easton, Pa., 1995 discloses various carriers used in formulating pharmaceutical compositions and known techniques for the preparation thereof.

Suitable pharmaceutical forms for oral administration include any solid composition (tablets, pastilles, capsules, granules, etc.) or liquid composition (solutions, bacterial suspensions, emulsions, syrups, etc.) and can contain conventional excipients known in the art, such as binding agents, for example syrup, acacia, gelatin, sorbitol, tragacanth, or polyvinylpyrrolidone; fillers, for example lactose, sugar, cornstarch, calcium fosfate, sorbitol or glycine; lubricants for the preparation of tablets, for example magnesium stearate, disintegrants, for example starch, polyvinylpirrolidone, sodium starch glycolate or microcrystalline cellulose; or pharmaceutically acceptable wetting agents such as sodium laurylsulfate.

The required dosage amount of the bacteria of the invention in the foodstuff or pharmaceutical composition will vary according to the nature of the disorder or the proposed use of the composition, whether used prophylactically or therapeutically and the type of organism involved.

Any suitable dosage of the bacteria of the invention may be used in the present invention provided that the toxic effects do not exceed the therapeutic effects. Therapeutic efficacy and toxicity may be determined by standard pharmaceutical procedures with experimental animals, such as by calculating the ED, (the dose therapeutically effective in 50% of the population) or LD (the dose lethal to 50% of the population) statistics. The dose ratio of toxic to therapeutic effects is the therapeutic index, which can be expressed as the LD/ED ratio. Nevertheless, the activity of the bacteria of the invention in the individual is naturally dose dependent as well as dependent on the metal nanoparticle load of the bacteria. Compositions which exhibit large therapeutic indices are preferred. The data obtained from animal studies are used to formulate a range of dosage for human or animal use. The dosage contained in such compositions is preferably within a range of circulating concentrations that includes the ED, with little or no toxicity. The dosage varies within this range depending upon the dosage form employed, the sensitivity of the patient, and the route of administration. The exact dosage will be determined by the practitioner, in light of factors related to the subject requiring treatment. For instance, for preparing a foodstuff according to the present invention the bacterium of the invention is incorporated in a suitable support, in an amount of from $10^5$ cfu/g to about $10^{12}$ cfu/g support material, preferably from about $10^6$ cfu/g to about $10^{11}$ cfu/g support material, more preferably from about $10^6$ cfu/g to about $10^{10}$ cfu/g support material.

In the case of a pharmaceutical composition, the dosage of the bacterium of the invention should be from about $10^5$ cfu/g to about $10^{14}$ cfu/g support material, preferably from about $10^6$ cfu/g to about $10^{13}$ cfu/g support material, more preferably from about $10^7$ cfu/g to about $10^{12}$ cfu/g support material. For the purpose of the present invention the abbreviation cfu shall designate a "colony forming unit" that is defined as the number of bacterial cells as revealed by microbiological counts on agar plates.

Dosage and administration are adjusted to provide sufficient levels of the metal nanoparticle or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Method for the Treatment and/or Prevention of Diseases Caused by a Metal Deficiency The bacterium of the invention is suitable to be used as oral supplement for a subject in need of a metal. The administration of a metal by means of the bacterium of the invention is advantageous, among other reasons, because the metal nanoparticle is specifically released in the intestine, avoiding the release of the metal in the stomach, which usually leads to unwanted side effects (example 2, FIG. 5). Moreover, different metals, such as calcium or zinc, associated to a lactic acid bacterium or a *bifidobacterium* are also released in both stomach and intestine conditions (example 2, FIGS. 6 and 7), which makes these bacteria suitable platforms for multimetal oral supplementation. Therefore, in another aspect, the invention relates to a bacterium selected from the bacterium of the first aspect and the bacterium obtainable by the method of the third aspect, or a biologically pure culture thereof for its use in the treatment and/or prevention of a disease or condition associated with a metal deficiency, wherein the bacterium comprises the metal that is deficient in said disease or condition and wherein the bacterium or culture is administered orally.

In another aspect, the invention relates to the use of a bacterium selected from the bacterium of the first aspect and the bacterium obtainable by the method of the third aspect, or a biologically pure culture thereof, in the manufacture of a medicament for the treatment and/or prevention of a disease or condition associated with a metal deficiency, wherein the bacterium comprises the metal that is deficient in said disease or condition and wherein the bacterium or culture is administered orally.

In another aspect, the invention relates to a therapeutic method for the treatment and/or prevention of a disease or condition associated with a metal deficiency, comprising administering to a subject a therapeutically effective amount of a bacterium selected from the bacterium of the first aspect and the bacterium obtainable by the method of the third aspect, or a biologically pure culture thereof, wherein the bacterium comprises the metal that is deficient in said disease or condition and wherein the bacterium or culture is administered orally.

The term "metal" has been defined in connection with the bacterium of the invention. In a particular embodiment of the method for the treatment and/or prevention of diseases caused by a metal deficiency, the metal is calcium or zinc. In a particular embodiment, the metal is a "metal cation". The term "metal cation", as used herein, refers to a metal element in a positive oxidation state, resulting in a positive electrical charge. In a particular embodiment, the metal cation is a divalent metal cation, that is, a metal cation with a valence of 2. Examples of divalent metal cations are $Fe^{2+}$, $Mn^{2+}$, $Co^{2+}$, $Ni^{2+}$, $Ca^{2+}$, $Zn^{2+}$, $Mg^{2+}$, $Cr^{2+}$, $Se^{2+}$ and $Si^{2+}$. In a particular embodiment, the divalent metal cation is $Ca^{2+}$ or $Zn^{2+}$.

In another particular embodiment of the method of treatment and/or prevention, the bacterium comprises more than one metal, for example, 2, 3, 4, 5 or more metals. In a more particular embodiment, the bacterium comprises calcium and zinc.

The lactic acid bacterium or *bifidobacterium* comprising at least one metal useful for the method for the treatment and/or prevention of diseases caused by a metal deficiency could be obtained contacting said lactic acid bacterium or *bifidobacterium* with said metal. An illustrative non limitative method for obtaining said bacteria comprising one or more metals is provided in the example 2 of the application.

In a particular embodiment, the metal is associated with the surface of the bacterium.

In another particular embodiment, the metal is comprised in a nanoparticle bound to the surface of the bacterium. The term "nanoparticle" as well as particular and preferred embodiments thereof has been previously described.

In a particular embodiment, the lactic acid bacterium or the bificobacterium comprises a metal nanoparticle, and at least one additional metal different from the metal comprised in the nanoparticle. Preferably, the metal nanoparticle comprises an oxide, more preferably iron oxide, even more preferably maghemite. Preferably, the at least one additional metal is selected from the group consisting of iron, manganese, cobalt, nickel, calcium, zinc, magnesium, potassium, copper, chromium, selenium, silicon, iodine and combinations thereof. More preferable, the additional metal is calcium, zinc selenium or a combination thereof. Even more preferably, the additional metal is calcium and zinc.

In a particular embodiment, when the metal is selenium it is not in the form of selenocysteine.

In a more particular embodiment, the lactic acid bacterium or *bifidobacterium* comprises a maghemite nanoparticle, calcium and zinc.

The term "treatment", as used herein, refers to any process, action, application, therapy, or the like, wherein a subject (or patient), including a human being, is provided medical aid with the object of improving the subject's condition, directly or indirectly, or slowing the progression of a condition or disorder in the subject, or ameliorating at least one symptom of the disease or disorder under treatment.

The term "prevention", as used herein, means that the bacterium of the invention is useful when administered to a patient who has not been diagnosed as possibly having the disorder or disease at the time of administration, but who would normally be expected to develop the disorder or disease or be at increased risk for the disorder or disease. According to the invention, the bacterium of the invention will slow the development of the disorder or disease symptoms, delay the onset of the disorder or disease, or prevent the individual from developing the disorder or disease at all.

The term "patient" or "subject", as used herein, refers to any animal, preferably a mammal and includes, but is not limited to, domestic and farm animals, primates and humans, for example, human beings, non-human primates, cows, horses, pigs, sheep, goats, dogs, cats, or rodents. In a preferred embodiment, the subject is a human being of any age or race. In a particular embodiment, the subject suffers from a disease associated with a metal deficiency. In another particular embodiment, the subject has not been diagnosed as suffering from a disease associated with a metal deficiency but is considered to be at increased risk of developing said disease.

The term "disease or condition associated with a metal deficiency" as used herein, refers to a condition presenting low serum levels of one or more metals. The serum levels of a metal that are considered low serum levels vary depending on parameters such as gender and age and are known by the person skilled in the art. The metal deficiency may stem from insufficient intake, digestion, absorption or utilization of said metal.

In a particular embodiment, the disease or condition associated with a metal deficiency is selected from the group consisting of a disease or condition associated with iron deficiency, a disease or condition associated with manganese deficiency, a disease or condition associated with cobalt deficiency, a disease or condition associated with nickel deficiency, a disease or condition associated with calcium deficiency, a disease or condition associated with zinc deficiency, a disease or condition associated with magnesium deficiency, a disease or condition associated with potassium deficiency, a disease or condition associated with copper deficiency, a disease or condition associated with chromium deficiency, a disease or condition associated with selenium deficiency, a disease or condition associated with silicon deficiency and a disease or condition associated with iodine deficiency.

Illustrative non-limitative examples of diseases or conditions associated with metal deficiencies are the following:
  Diseases or conditions associated with iron deficiency: weakness, fatigue, skin pallor shortness of breath, anemia, low auto-immunity, depression, low blood pressure, speech disorders, poor memory and colds.
  Diseases or conditions associated with manganese deficiency: attention deficit-hyperactivity disorder (ADHD), asthma, carpal tunnel syndrome, seizures, loss of libido, miscarriage, growth retardation and nightmares.

Diseases or conditions associated with cobalt deficiency: pernicious anemia, severe fatigue, shortness of breath and low thyroid.

Diseases or conditions associated with nickel deficiency: hyperglycemia (high blood sugar), low blood pressure, depression, liver disease, anemia, low stomach acid, sinus congestion, fatigue and low adrenals.

Diseases or conditions associated with calcium deficiency: rickets, osteomalacia, osteoporosis, receding gums, pre-menstrual syndrome, panic attacks, muscle cramps, weak lungs, lower back pain, kidney stones, insomnia, weak bones, bone spurs and calcium deposits.

Diseases or conditions associated with zinc deficiency: loss of taste, loss of smell, retarded growth, delayed sexual development, slow wound healing, ADHD, hair loss, birth defects, body odor, brain disorders, diarrhea, heart defects, hernia, impotence, lung disorders and prostate disorders.

Diseases or conditions associated with magnesium deficiency: muscle weakness and cramps, nausea, cardiac arrhythmias, ADHD, arterial calcification, low calcium absorption, convulsions, depression, gastrointestinal disorders, growth disorders, menstrual migraines, osteoporosis, tremors, moodiness and fainting.

Diseases or conditions associated with potassium deficiency: nausea, anorexia, irritability, muscle weakness, fear, mental illness, low energy, aches and twinges, acidity, tendency toward violence, suspiciousness, loss of ambition, nervousness and negativity.

Diseases or conditions associated with copper deficiency: ADHD, anemia, arthritis, violent, cerebral palsy, high cholesterol, drooping eyelids, white hair, hernia, liver, cirrhosis, learning problems, low blood sugar, high risk of stroke and varicose veins.

Diseases or conditions associated with chromium deficiency: ADHD, unexpected weight loss, low sperm count, diabetes, manic depression, learning problems, growth problems, hyperactivity, coronary vessel disease, cataracts and abnormal sugar levels.

Diseases or conditions associated with selenium deficiency: age spots, skin aging, Alzheimer's disease, cancer, cystic fibrosis, fatigue, heart palpitations, HIV, hypothyroidism, liver damage, muscle weakness and scoliosis.

Diseases or conditions associated with silicon deficiency: brittle hair, brittle fingernails and toenails, poor skin quality, poor calcium utilization and arterial disease.

Diseases or conditions associated with iodine deficiency: goiter, menstrual disorders, mental confusion, heart and lung problems.

According to the first therapeutic use of the invention, a metal nanoparticle comprising the metal which is deficient in the disease or condition to be treated is administered to the subject in need thereof. For example, if a subject is going to be treated from a disease related with iron deficiency, or if the prevention of a disease associated with iron deficiency is desirable in a subject in risk of developing said disease, a bacterium comprising an iron nanoparticle is administered to this subject.

According to the first therapeutic uses and methods of the invention, the bacterium or the biologically pure culture is administered orally.

The term "oral administration", as used herein, refers to any form of delivery of the bacterium or culture of the invention to a subject, wherein the bacterium or culture of the invention is placed in the mouth of the subject, whether or not the bacterium or culture of the invention is immediately swallowed. Thus "oral administration" includes buccal and sublingual as well as esophageal administration.

The term "therapeutically effective amount", as used herein, refers to the sufficient amount of the bacterium or culture of the invention to provide the desired effect and will generally be determined by, among other causes, the characteristics of the bacterium or culture of the invention itself and the therapeutic effect to be achieved. It will also depend on the subject to be treated, the severity of the disease suffered by said subject, the chosen dosage form, etc. For this reason, the doses mentioned in this invention must be considered only as guides for the person skilled in the art, who must adjust the doses depending on the aforementioned variables. In an embodiment, the effective amount produces the amelioration of one or more symptoms of the disease that is being treated, for example, the normalization of the levels of the metal that was deficient in the subject.

Methods for the Treatment of Cancer

The bacteria according to the invention or the biologically pure cultures according to the invention are also suitable for delivering magnetic nanoparticles to the gastrointestinal tract. The arranged magnetic nanoparticles onto the bacteria surface make that the bacteria exhibit permanent magnetic moments and stronger magnetic response. In an applied alternating magnetic field, magnetic moments of magnetic nanoparticles could be periodically reoriented, leading to the conversion of magnetic energy into thermal energy, and the temperature of surrounding regions was quickly elevated to the therapeutic temperature range (higher than 42° C.), which would result in the killing by hyperthermia of the neighbouring cells.

Thus, in another aspect, the invention relates to a bacterium according to the first aspect or to a bacterium obtainable by the method of the third aspect or to a biologically pure culture thereof for its use in the treatment of cancer, wherein the metal is comprised in a magnetic nanoparticle.

In another aspect, the invention relates to the use of a bacterium according to the first aspect or to a bacterium obtainable by the method of the third aspect or to a biologically pure culture thereof in the manufacture of a medicament for the treatment of cancer, wherein the metal is comprised in a magnetic nanoparticle.

In another aspect, the invention relates to a therapeutic method for the treatment of cancer, comprising administering to a subject a therapeutically effective amount of a bacterium according to the first aspect or to a bacterium obtainable by the method of the third aspect or to a biologically pure culture thereof, wherein the metal is comprised in a magnetic nanoparticle.

The terms "treatment", "subject" and "therapeutically effective amount" have been previously defined in connection with the therapeutic uses and methods for the treatment and/or prevention of diseases associated with metal deficiency.

The term "cancer", as used herein, refers to a disease characterized by uncontrolled cell division (or by an increase of survival or apoptosis resistance), by the ability of said cells to invade other neighbouring tissues (invasion) or by the spread to other areas of the body where the cells are not normally located (metastasis) through the lymphatic and blood vessels. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastrointestinal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodglun's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; slun cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill in the art.

In a particular embodiment, the cancer is a gastrointestinal cancer. The term "gastrointestinal cancer", as used herein, refers to any cancer affecting the gastrointestinal tract, including the esophagus, stomach, biliary system, pancreas, small intestine, large intestine or colon and rectum. In a particular embodiment, the gastrointestinal cancer is a stomach cancer, a small intestine cancer or a large intestine or colon cancer.

According to the therapeutic methods and uses for the treatment of cancer, the bacterium of the invention can be administrated by any suitable route, for example, oral route, parenteral route or intravenous route. In a preferred embodiment, the bacterium or culture of the invention are administrated orally. The term "oral administration" has been previously defined.

In a particular embodiment of the therapeutic methods and uses for the treatment of cancer, the bacterium according to the first aspect is capable of being transferred to the mammary gland after oral intake. Methods for detecting the ability of a bacterium to being transferred to the mammary gland have been previously disclosed in connection with the bacterium of the first aspect, as well as examples and particular embodiments of said bacteria. In this particular embodiment, the bacterium of the invention is useful for the treatment of a breast cancer. Thus, in a particular embodiment of the therapeutic method and uses of the invention, the cancer is breast cancer and the bacterium is a bacterium capable of being transferred to the mammary gland after oral intake.

The term "breast cancer" refers to any malignant proliferative mammary cell disorder, usually occurring in the ducts (the tubes that carry milk to the nipple) and lobules (milk producing glands).

In a particular embodiment, the therapeutic method for the treatment of cancer comprises the step of targeting the bacterium according to the first aspect to the tumor.

The step of targeting the bacterium according to the invention to a tumor could be performed by different mechanisms. In one embodiment, the bacterium is directed to the tumor due to its preference for tumor anaerobic microenvironment. In another embodiment, the bacterium comprising a magnetic nanoparticle, previously defined, is guided and pulled towards the target tumor by one or more magnetic fields or magnetic field gradients (e.g., an external source of magnetic fields or magnetic field gradients). Such fields or gradients can be generated by, for example, one or more magnets and associated medical devices placed within or adjacent to a target tumor prior to, during or after bacterium delivery. In some embodiments, the magnets are placed inside the body using surgical or percutaneous methods inside the target tumor, or outside the target tumor (e.g., around or adjacent to the target tumor). In some embodiments, the magnets are external magnets that are placed outside of a subject's body to create an external source of magnetic field around or adjacent to the target tumor. In some embodiments, the source of magnetic fields is a permanent magnet (e.g., neodymium (NdFeB) magnet). In one embodiment, the source of magnetic fields is an electromagnet. In other embodiments, the size of magnets ranges from about 1 mm to about 10 m and the strength of magnetic fields ranges from about 0.1 Tesla to about 100 Tesla, including about 0.1 to about 0.5 Tesla, about 0.5 to about 1 Tesla, about 1 Tesla to about 1.1 Tesla, about 1.1 Tesla to about 1.2 Tesla, about 1.2 Tesla to about 1.3 Tesla, about 1.3 Tesla to about 1.4 Tesla, about 1.4 Tesla to about 1.5 Tesla, about 1.5 Tesla to about 2 Tesla, about 2 Tesla to about 4 Tesla, about 4 Tesla to about 10 Tesla, about 10 Tesla to about 30 Tesla, about 30 Tesla to about 50 Tesla, about 50 Tesla to about 70 Tesla, about 70 Tesla to about 90 Tesla, and overlapping ranges thereof. In several embodiments, the magnetic field is applied for a time period ranging from about 1 minute up to about 5 hours. In some embodiments, the magnetic field is applied for about 1 minute to 5 minutes, about 5 minutes to about 10 minutes, about 10 minutes to about 20, about 20 minutes to about 30 minutes, and overlapping ranges thereof. In several embodiments, the magnetic field is applied for about 5-15 minutes, including about 6, 7, 8, 9, 10, 11, 12, 13, or 14 minutes.

In some embodiments, the source of magnetic fields is from one or more magnets of an apparatus (e.g., a group of magnets as an integral apparatus to shape and focus the magnetic field). Such apparatus can include, for example, a surgical tool (e.g., catheters, guidewires, and secondary tools such as lasers and balloons, biopsy needles, endoscopy probes, and similar devices) with a magnetic tip attachment (see, e.g., U.S. Pat. No. 7,280,863 and U.S. Pat. Publ. Nos. 200711116006, 2006/0116634, 2008/0249395, 2006/0114088 and 2004/0019447). Thus, in some embodiments, bacteria are delivered and an external magnet is used to target the bacteria.

When the bacterium of the invention comprises a magnetic nanoparticle, said bacterium could be used to apply a heat therapy to a tumor, preferably a solid tumor, by means of an alternating magnetic field applied in the proximity of the tumor. In this embodiment, once the magnetic nanoparticle-loaded bacterium has reached the tumor, an alternative magnetic field is applied in the proximity of the tumor, resulting on heat production by the magnetic nanoparticle-loaded bacterium. This heat treatment induces the partial or total destruction of the tumor cells and/or of the tumor(s).

Since tumor cells are more susceptible to heat than healthy cells (See for example: Overgaard et al., Cancer, 1977, 39, 2637-2646), the thermotherapy described in this disclosure could selectively destroy tumor cells. Thus, in a particular embodiment, the therapeutic method comprises the step of
i) targeting the bacterium according to the first aspect comprising a magnetic nanoparticle to a tumor and
ii) applying an alternative magnetic field around or adjacent the tumor.

The term "alternative magnetic field" or "oscillating magnetic field", as used herein, refers to a magnetic field whose intensity changes over time. In one embodiment, the alternative magnetic field applied during the treatment is characterized by a frequency lying between about 50 k Hz and about 1000 k Hz, preferably between about 100 k Hz and about 500 k Hz, more preferably between about 100 kHz and about 200 k Hz.

In another embodiment, the magnetic field is characterized by a strength lying between about 0.1 mT and about 200 mT, preferably between about 1 mT and about 100 mT, more preferably between about 10 mT and about 60 mT, typically between about 10 mT and about 50 mT.

The maximum value of the magnetic field strength is determined by the value at which it becomes toxic for the organism (i. e. essentially when it generates Foucault's currents). It may be possible that magnetic fields of strengths higher than 200 mT can be used in the therapy if they are shown to be non-toxic.

In another embodiment, the method of the present invention is characterized by the length of time during which the magnetic field is applied. This length of time may be between about 1 second and about 6 hours, preferably between about 1 minute and about 1 hour, preferably between 0.5 and 30 minutes, most preferably between 1 minute and 30 minutes.

The heat treatment is preferably applied to anesthetized patients. Therefore, the time during which the treatment is carried out may be equal or less than the length of time of the anesthesia. A heat treatment can thus potentially be carried out during more than 6 hours, for example if a patient is anesthetized during more than 6 hours.

In another embodiment, the method of the present invention is characterized by the quantity of magnetic nanoparticle-associated bacteria used during the therapy. This quantity of magnetic nanoparticle-associated bacteria is related to the magnetic nanoparticle load of the bacteria and to the magnetic material load of the nanoparticle. This quantity is estimated by measuring the amount of magnetic material present in the suspension of magnetic nanoparticle-associated bacteria, which is administered. The quantity of magnetic nanoparticle-associated bacteria, which needs to be injected, essentially depends on the volume of the treated tumor, the temperature required during the treatment and the method of injection. The largest tumor volume and the highest tumor temperature require the largest quantity of magnetic nanoparticle-associated bacteria administered.

In another embodiment, the concentration of the suspension of magnetic nanoparticle-associated bacteria typically lays between 1 mg/ml and 100 mg/ml, preferably between 10 mg/ml and 50 mg/ml, where this concentration represents the quantity of magnetic material, preferably iron oxide, more preferably maghemite, contained within the suspension.

In another embodiment, the administration of the magnetic nanoparticle-associated bacteria to the subject is repeated. The number of repetition depends on the quantity of magnetic nanoparticle-associated bacteria, which is administered at once. If only a small quantity of magnetic nanoparticle-associated bacteria is administered at once, the administration step might be repeated several times until the desired amount of magnetic nanoparticle-associated bacteria is administered to a patient.

In another embodiment the heat treatment started by application of the alternative magnetic field is repeated. The successive heat treatments applied after administration of a given amount of magnetic nanoparticle-associated bacteria are called a heat cycle.

The given amount of magnetic nanoparticle-associated bacteria used for each heat cycle may have been administered through a single administration or through several successive administrations as explained above. The different heat treatments within a heat cycle are separated one from another by a resting time. The resting time may be equal to 1 second or longer than 1 second, preferably equal to 1 minute or longer than 1 minute, more preferably equal to 10 minutes or longer than 10 minutes, preferably equal to or longer than 30 minutes.

In an embodiment, the different heat treatments within a heat cycle are separated one from another by a longer resting time than that mentioned above. This resting time may lie between 1 day and 15 days.

In an embodiment, the heat cycle is repeated 1 to 648 000 times, in particular 1 to 10 1000 times, more particularly 1 to 100 times, typically 1 to 10 times. The highest repetition rate of 648 000 times is estimated by assuming that the treatment is carried out for a very short time, typically about one second, during 15 days with a very short resting time, typically about one second resting time separating each treatment. The number of repetition of the treatment depends on the length of time of the treatment. Preferentially the longer the treatment is the less repetition is needed provided the other parameters of the therapy (such as the strength and or frequency of the applied magnetic field) are fixed.

The transformation of magnetic energy to thermal ablation has been widely demonstrated to induce the drug delivery with spatial and temporal control depending on the 'on-off' operations of the applied high-frequency magnetic field (J. Liu, Y. Zhang, C. Wang, R. Xu, Z. Chen, N. Gu, J. Phys. Chem. C 114 (2010) 7673-7679). As an example, magnetite nanoparticles with ibuprofen in polymer polyvinyl alcohol (PVA) and pluronic F68, and a thin layer of silica exhibits fast magnetically-triggered drug release behavior (S. H. Hu, Y. Y. Chen, T. C. Liu, T. H. Tung, D. M. Liu, S. Y. Chen, Chem. Commun. 47 (2011) 1776-1778). Therefore, in another embodiment, the bacterium of the invention comprising a magnetic nanoparticle further comprises a therapeutic agent useful in the treatment of cancer. In one embodiment the agent is encoded on a vector capable of expressing at least one exogenous gene encoding said agent. In this embodiment, the bacterium of the invention is transformed with the vector. In a further embodiment the agent is linked to the bacterium of the invention. The agent may be linked, bonded, fixed or chemically coupled or attached to the bacterium of the invention or to the bacterium membrane or attached/linked by any other means known to the skilled person. In a further embodiment, the agent is linked to the metal nanoparticle or encapsulated in the metal nanoparticle. The method for linking the agent to the metal nanoparticle or for encapsulating the agent into the metal nanoparticle will depend on the nature of the agent, and is known by the person skilled in the art.

The term "therapeutic agent useful in the treatment of cancer", as used herein, refers to an agent suitable for being used in the treatment of cancer, such as a cytotoxic agent, an antiangiogenic agent or an antimetastatic agent.

Cytotoxic agents which can be used according to this embodiment of the therapeutic method of the invention for the treatment of cancer include but are not limited to anthracycline antibiotics such as doxorubicin and daunorubicin, taxanes such as Taxol™ and docetaxel, vinca alkaloids such as vincristine and vinblastine, 5-fluorouracil (5-FU), leucovorin, irinotecan, idarubicin, mitomycin C, oxaliplatin, raltitrexed, tamoxifen, cisplatin, carboplatin, methotrexate, actinomycin D, mitoxantrone, blenoxane or mithramycin. Antiogiogenic agents which can be used in combination with the antibodies of the invention for the treatment of cancer include but are not limited to an antiangiogenic agent selected from the group of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, penicillamine, PTK787/ZK 222584, RPI.4610, squalamine lactate, SU5416, thalidomide, combretastatin, tamoxifen, COL-3, neovastat, BMS-275291, SU6668, anti-VEGF antibodies, Medi-522 (Vitaxin II), CAL interleukin 12, IM862, amiloride, angiostatin, K1-3 angiostatin, K1-5 angiostatin, Captopril, DL-alpha-difluoromethylornithine, DL-alpha-difluoromethylornithine HCl, endostatin, fumagillin, herbimycin A, 4-hydroxyphenylretinamide, juglone, laminin, laminin hexapeptide, laminin pentapeptide, lavendustin A, medroxyprogesterone, minocycline, placenta ribonuclease inhibitor, suramin, thrombospondin, antibodies directed against proangiogenic factors (for example, Avastin, Erbitux, Vectibix, Herceptin); low molecular weight tyrosine kinase inhibitors of proangiogenic growth factors (for example Tarceva, Nexavar, Sutent, Iressa); mTOR inhibitors (for example Torisel); interferon alpha, beta and gamma, IL-12, matrix metalloproteinase inhibitors (for example, COL3, marimastat, batimastat); ZD6474, SU11248, vitaxin; PDGFR inhibitors (for example Gleevec); NM3 and 2-ME2; cyclopeptides such as cilengitide. Antimetastatic agents which can be used in combination with the antibodies of the invention for the treatment of cancer include but are not limited to any agent capable of acting as an antimetastatic agent, such as alkylating agents; antimetabolites such as 5-fluorouracil, pemetrexed (MTA), raltitrexed (TDX); platinum cytotoxic agents such as cisplatin or oxaliplatin; topoisomerase inhibitors; antimicrotubule agents; anthracyclines; plant alkaloids; GTPase inhibitors; angiogenesis inhibitors; matrix metalloproteinase inhibitors; inhibitors of the cell cycle regulating kinase, such as cyclin-dependent kinases and cyclin inhibitors; Wnt signaling inhibitors; inhibitors of the E2F transcription factor; histone deacetylase inhibitors; AKT kinase or ATPase inhibitors.

Non-Therapeutic Method

The association between the metal nanoparticle and the lactic acid bacterium or *bifidobacterium*, which is stable under stomach pH conditions, is broken due to relatively high pH value in the intestine. This results in the release of the metal nanoparticle in the intestinal tract (example 2). Moreover, different metals, such as calcium or zinc, associated to a lactic acid bacterium or a *bifidobacterium* are also released in both stomach and intestine conditions (example 2, FIGS. 6 and 7). Therefore, the bacterium of the invention, when orally administered, is useful for the delivery of a compound of interest in the intestine of a subject.

Thus, in another aspect, the invention also relates to a non-therapeutic method for the delivery of a metal in the intestine of a subject, comprising the oral administration of the bacterium of the first aspect or the bacterium obtainable by the method of the third aspect or a biologically pure culture thereof.

The term "non-therapeutic method", as used herein, refers to a process, action, application or the like on a subject that (i) is not directed to the improvement of a condition or disease, directly or indirectly, or to slowing the progression of a condition or disease, or to ameliorating one or more symptoms of a condition or disease of said subject and (ii) is not directed to delay the onset of the disorder or disease, or prevent the individual from developing the disorder or disease at all.

Thus, the subject according to the non-therapeutic method of the invention does not suffer from a disease or condition related with a metal deficiency or any other disease of condition that could be treated by administering the bacterium or the culture of the invention and is not at increased risk of developing said diseases The terms "metal" and "oral administration" have been previously defined in connection with the therapeutic methods of the invention.

The term "intestine" or "bowel", as uses herein, refers to the segment of the digestive tract extending from the pyloric sphincter of the stomach to the anus. The term intestine includes both the small intestine, which in turns comprises the duodenum, jejunum and ileum, and the large intestine, comprising the cecum and colon.

Imaging Agent and Method for Imaging

The bacterium of the invention is capable of contrasting the digestive tract on an imaging method, such as magnetic resonance (example 4). Therefore, in another aspect, the invention relates to a contrast agent comprising a bacterium according to the first aspect or a bacterium obtainable by the method of the third aspect or a biologically pure thereof, wherein the metal is comprised in a magnetic nanoparticle.

The terms "imaging agent" and "contrast agent" are used here interchangeably and refer to a biocompatible compound the use of which facilitates the differentiation of different parts of the image, by increasing the "contrast" between those different regions of the image. Preferably, the contrast agent is a contrast agent for magnetic resonance image (MRI). Contrast agent for magnetic resonance imaging includes gadolinium chelates, manganese chelates, chromium chelates and iron particles. MRI contrast agents can include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

In a particular embodiment, the contrast agent comprises a bacterium comprising a metal nanoparticle comprising iron, more preferable iron oxide, even more preferably maghemite.

In another embodiment, the invention relates to the use of a bacterium according to the first aspect or a bacterium obtainable by the method of the third aspect or to a culture thereof as a contrast agent for magnetic resonance imaging.

In a particular embodiment the bacterium according to the first aspect or the bacterium obtainable by the method of the third aspect or the culture thereof can be administered orally or intravenously for their use as contrast agents for magnetic resonance imaging.

The term "magnetic resonance imaging" or "MRI", as used herein, refers to a medical imaging technique most commonly used in radiology to visualize the structure and function of the body. It provides detailed images of the body in any plane. MRI uses no ionizing radiation, but uses a powerful magnetic field to align the nuclear magnetization of (usually) hydrogen atoms in water in the body. Radiofrequency fields are used to systematically alter the alignment of this magnetization, causing the hydrogen nuclei to produce a rotating magnetic field detectable by the scanner. This signal can be manipulated by additional magnetic fields to build up enough information to construct an image of the body. When a subject lies in a scanner, the hydrogen nuclei (i.e., protons) found in abundance in an animal body in water molecules, align with the strong main magnetic field. A second electromagnetic field that oscillates at radiofrequencies and is perpendicular to the main field, is then pulsed to push a proportion of the protons out of alignment with the main field. These protons then drift back into alignment with the main field, emitting a detectable radiofrequency signal as they do so. Since protons in different tissues of the body (e.g., fat versus muscle) realign at different speeds, the different structures of the body can be revealed. Contrast agents may be injected intravenously to enhance the appearance of blood vessels, tumors or inflammation. MRI is used to image every part of the body, but is particularly useful in neurological conditions, disorders of the muscles and joints, for evaluating tumors and showing abnormalities in the heart and blood vessels.

The bacterium according to the first aspect or the bacterium obtainable by the method of the third aspect could be used as a contrast agent for the magnetic resonance imaging of virtually any part of the body. Without wanting to be bound by any particular theory, both lactic acid bacteria and bifidobacteria are reported to be attracted by hypoxic tumor environments and, consequently, these bacteria are especially useful for the imaging of solid tumors.

In a particular embodiment, the bacterium according to the first aspect or the bacterium obtainable by the method of the third aspect or the culture thereof is used as a contrast agent for magnetic resonance imaging of the digestive tract. The term "digestive tract", as used herein, refers to a series of hollow organs joined in a long, twisting tube from the mouth to the anus. The digestive tract includes the mouth, esophagus, stomach, small intestine, large intestine or colon and rectum.

In another embodiment, the invention relates to a method for the magnetic resonance imaging of the digestive tract of a subject which comprises:
 (i) orally administering to said subject a bacteria according to the first aspect, a bacterium obtainable by the method of the third aspect, a culture thereof or a contrast agent according to the invention, wherein the metal is comprised in a nanoparticle and
 (ii) detecting the metal nanoparticles in the digestive tract of the subject.

The terms "magnetic resonance imaging", "digestive tract", "subject", "oral administration" have been previously defined.

The step of detecting the metal nanoparticles in the digestive tract of the subject can be done by a person skilled in the art, preferably a specialized facultative or technician, by scanning with RMI equipment.

The part of the digestive tract that can be contrasted by the imaging method of the invention will depend on the time elapsed between the oral administration of the bacterium or culture of the invention and the detection of the metal nanoparticles by scanning the digestive tract of the subject. Therefore, in one embodiment of the magnetic resonance imaging method, the scanning is carried out between 1 and 5 hours after the oral administration, preferably 3 hours after the oral administration, thereby imaging the stomach or between 6 and 24 hours after the oral administration, preferably 24 hours after the oral administration, thereby imaging the intestine.

The invention is described by way of the following examples, which are merely illustrative and no limitative of the scope of the invention.

Example 1

Artificial Magnetic Bacteria as Nanomagnets at Room Temperature

Materials and Methods
Preparation of Bacteria with Maghemite Nanoparticles

A culture of bacteria was prepared and kept at 37° C. and agitation for 24 h. Then the bacterial culture was kept on ice to cool bacteria down, bacteria were collected by centrifuging at 100 g and the optical density was measured at 600 nm to take $1 \times 10^9$ cfu/ml. Bacteria were resuspended carefully in 1 ml of ice-cold MgCl2-CaCl2 solution (174.02 g of CaCl2.2H2O and 203.02 g of MgCl2.6H2O and dissolve them in 1 L of distilled water) to wash away all impurities and bacteria were collected at 3000 g, 10 min After this, tubes were kept in inverted position for 1 min for water to drain away and then 66.6 µl of a solution of the maghemite nanoparticles (0.95M) at pH 2 were mixed with the bacteria. The mixture was filled with water up to 1 ml and bacteria were collected by centrifuging at 100 g, 20 min, to remove the excess of ion.

Maghemite nanoparticles were prepared according to Massart's method (Massart, R. IEEE Trans. Magn. 1981, 1247-1248) by coprecipitation of Fe(II) and Fe(III) salts in stoichiometry of 0.5. By adjusting both pH (12 and 11 for 4 and 6 nm, respectively) and ionic strength (2 and 1 M $NaNO_3$ for 4 and 6 nm, respectively), the size of the resulting magnetite nanoparticles can be controlled (Vayssieres, L.; Chaneac, C.; Tronc, E.; Jolivet, J. P. J. Colloid Interface Sci. 1998, 205, 205-212). All solutions were carefully deaerated with argon. After oxidation, a colloid of maghemite nanoparticles stable at pH 2 was obtained.
Results Herein, we report a simple and efficient methodology to synthesize artificial magnetic bacteria by the deposition of magnetic nanoparticles on a biological platform as it is the surface of gram positive bifidobacteria. The negative charge of the external bacteria surface and the positive one of nanoparticles allow interaction. The possibility of this electrostatic interaction may require the presence of the EPS biofilms. More interestingly, it is also shown that the orientation and manipulation of the as-formed artificial magnetic bacteria by an external magnetic field it is also possible. Moreover, the magnetic orientation occurs at room temperature, a fact that envisages diverse and attractive applications in different recording magnetic devices. The methodology involves mild conditions and may be adapted to large-scale fabrication, which allow the production of cheaper, more environmentally friendly components for devices of the future.

Deposition is driven by the electrostatic interactions existing between positive maghemite nanoparticles (8 nm-sized) and the whole external surface of bifidobacteria. The physical interaction is controlled by changing the charge of the maghemite nanoparticles surface, so that the adsorption level of maghemite nanoparticles into the bifidobacteria displays distinct and highly controllable attachment level. FIG. 1 shows the particle density distribution as a function of the magnetic nanoparticle surface charge. As it can be observed, positive maghemite nanoparticles selectively attach to the peptidoglycan shell (a) whereas negative ones exhibit no affinity for deposition (b).

Figure 2:
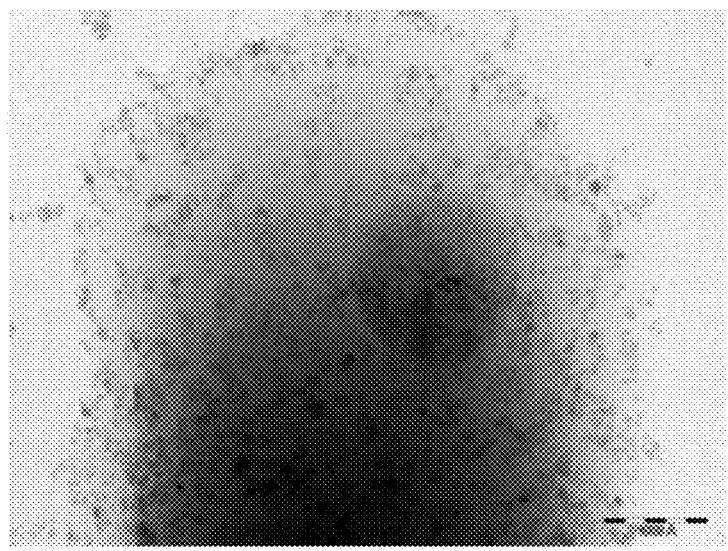
FIG. 2. A typical non contrasted TEM image of bifidobacteria after incubation with positive maghemite nanoparticles forming like a plum pudding.

The most favourable conditions were observed when *Bifidobacterium breve* in MRS medium were incubated with 8-nm sized maghemite nanoparticles at pH 2 to afford red homogeneous solutions that were centrifuged and washed with a NaCl solution for five times. The solutions were examined by Transmission Electron Microscopy (TEM). A typical image obtained from the material shows discrete electron-dense cores, which are regular in shape and size (FIG. 2).

The mean diameter was statistically measured to be 8±0.5 nm. Energy dispersive spectroscopy confirmed that the particles contained Fe, which was not detected outside the particles.

Large accumulation of magnetic nanoparticles takes place on the external shell of bacteria forming like a plum pudding, where the magnetic nanoparticles are positively-charged "plums" surrounded by a negatively-charged "pudding", formed by the peptidoglycan network.

Figure 3:
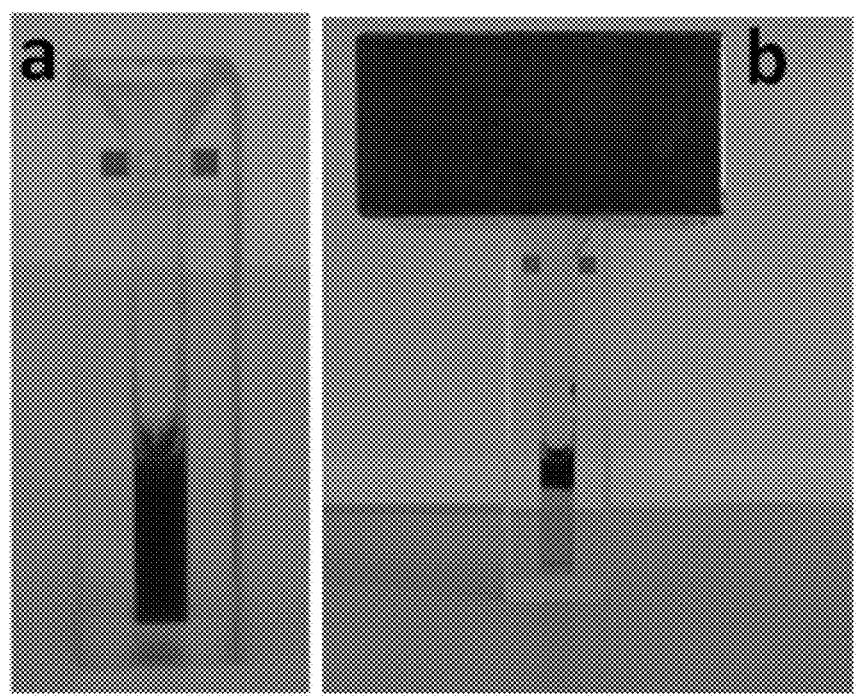
FIG. 3. (a) Dispersion of artificial magnetic bacteria in the aqueous media followed by (b) separation of the magnetic bacteria by a magnetic field.

The bacteria labeled with maghemite nanoparticles are easily dispersed in water forming a red-dark solution. Centrifugation followed by washing does not remove the nanoparticles from the bacteria surface, pointing out the strong interaction between nanoparticles and the peptidoglycan network. Magnetic bacteria are easily oriented in low magnetic fields and can be removed from solutions by small permanent magnets (FIG. 3). The orientation in low magnetic fields at room temperature was unexpected as it has been shown that only maghemite nanoparticles larger than 20 nm are attracted from solution by modest magnetic gradients. The fact that the magnetic bacteria behave as magnets at room temperature points out the existence of a magnetic long order, due to dipolar-dipolar interaction as a consequence of the large accumulation and short distances among nanoparticles at the peptidoglycan shell. In this sense, it is interesting to note that the bottom yellow solution obtained after magnet application (FIG. 3b) only contained maghemite nanoparticles did not move with the application of an external magnetic field, that is the 8 nm maghemite nanoparticles are not attracted by the permanent magnet.

Moreover, the bottom yellow solution obtained after magnet separation (FIG. 3b) is free of bacteria. This demonstrates that i) all bacteria were labeled with magnetic nanoparticles, ii) the bacteria act as bioplatforms where magnetic long order between 8 nm-sized maghemite nanoparticles takes place.

Figure 4:
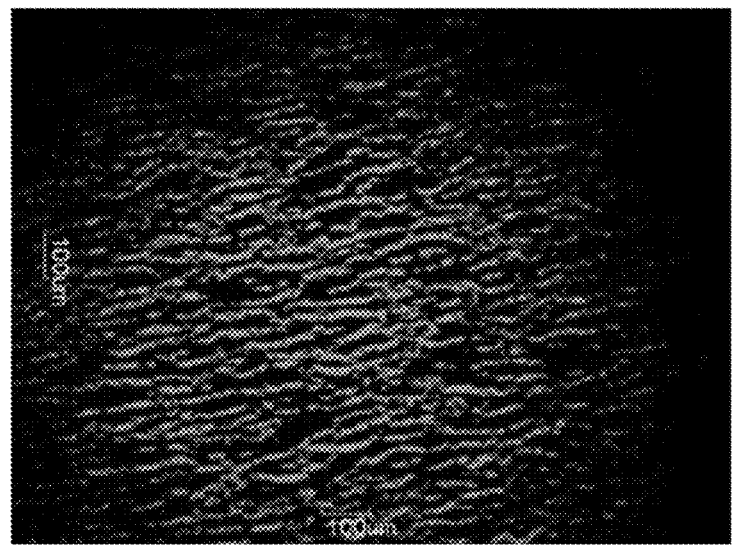
FIG. 4. Deposition of artificial magnetic bacteria labeled with a dye on polylysine in the presence of an external magnet.

Since these magnetic bacteria can move in the presence of a low magnetic gradient field at room temperature, we assayed the formation of magnetically oriented film by the application of an external magnetic field to a single drop of artificial magnetic bacteria deposited on different substrates. In order to visualize the magnetic bacteria, these were previously labeled with a fluorescent dye, which is commonly used for labeling live bacteria. As an example FIG. 4 shows the effect of a modest permanent magnet on the artificial magnetic bacteria when deposited on polylysine glass.

Fluorescent artificial magnetic bacteria behave as magnets at room temperature and are aligned following the external magnetic field lines giving rise to a nanostructured organization of magnetic bacteria where position and orientation of nanoobjets are controlled by an external input (the magnetic field).

In conclusion, the present invention shows the possibility of preparing artificial magnetic bacteria and the possibility of controlling the magnetic orientation of these nanoobjects at room temperature. This step is crucial in the use of this system in recording magnetic devices.

Example 2

Iron, Calcium and Zinc Delivery Study

Materials and Methods
Bacteria with Minerals (Adapted from Sambrook J, Russell D W (2001). Molecular Cloning: A Laboratory Manual. 3rd Ed. Cold Spring Harbor (N.Y.): Cold Spring Harbor Laboratory Press. 132-150)

A batch of four different types of samples was prepared: a) Only bacteria (control), b) bacteria with calcium, c) bacteria with calcium and zinc and finally d) bacteria with calcium, zinc and iron.

The general procedure is as follows:
1. Measure the $O.D._{600}$ of the 24 hours *L. fermentum* culture to collect $2 \times 10^9$ cells/ml.
2. Cool the cultures to 0° C. by storing the tubes on ice for 10 minutes.
3. Recover the cells by centrifugation at 3000 g, 20 minutes at 4° C.
4. Decant the medium from the cell pellets. Stand the tubes in an inverted position on a pad of paper towels for 1 minute to allow the last traces of media to drain away.
5. Resuspend each pellet by swirling or gentle vortexing in 1 ml of ice-cold $MgCl_2$—$CaCl_2$ solution (174.02 g of $CaCl_2$).$2H_2O$ and 203.02 g of $MgCl_2.6H_2O$ and dissolve them in 1 L of distilled water).
6. Recover the bacteria by centrifugation at 3000 g for 20 minutes at 4° C.
7. Decant the medium from the cell pellets. Stand the tubes in an inverted position on a pad of paper towels for 1 minute to allow the last traces of media to drain away.
8. Resuspend the pellet by swirling or gentle vortexing in 1 ml of ice-cold 0.5 M $CaCl_2$).
9. Add 5 µl $Zn(NO_3)_2.4H_2O$ (1M).
10. Recover the bacteria by centrifugation at 3000 g for 20 minutes at 4° C.
11. Add 100 µl of maghemite nanoparticles (0.95 M, pH 2-5) to the isolated pellet.
    Note 1: when preparing control with only bacteria (control), after step 7, resuspend the pellet by swirling or gentle vortexing in 1 ml distilled water and then jump up to step 11.
    Note 2: when preparing bacteria with only $CaCl_2$ remove steps 9 and 10.
    Note 3: when preparing bacteria with $CaCl_2$ and Zinc remove step 11.
    Note 4: when preparing bacteria with $CaCl_2$, zinc and iron, the sequence followed to add minerals was, calcium, zinc and iron.
12. Transfer the tubes to a rack placed in a preheated 42° C. circulating water bath. Store the tubes in the rack for exactly 90 seconds. Do not shake the tubes.
13. Rapidly transfer the tubes to an ice bath. Allow the bacteria to chill for 1-2 minutes.
14. Recover the bacteria by centrifugation at 3000 g for 20 minutes at 4° C.
15. Wash the bacteria twice in distilled water.

The resulting bacterium samples were incubated in both gastric and gastrointestinal juice at 37° C. with continuous agitation (170 rpm). 1 ml of sample was taken every hour to complete 6 hours in the case of the gastric juice simulation and 4 hours in the case of the gastrointestinal juice simulation. The metal release was analyzed by atomic absorption and ICP (inductively coupled plasma mass spectrometry).

Simulated Gastric Juice Composition:

Simulated gastric juice was prepared by dissolving pepsin (0.01 g), gastric mucin (0.015 g) and NaCl (0.088 g) in 10 ml distilled water with pH of 1.3 adjusted using 1M HCl.

The final composition of the sample in the reaction cell was therefore, 1 mg/ml of pepsin, 1.5 mg/ml of gastric mucin and 8.8 mg/ml of Nacl (0.15 mM).

Simulated Gastrointestinal Juice Composition:

Simulated gastrointestinal juice was prepared by dissolving bile extract (0.05 g), lipase (0.016 g) and CaCl2 (0.007 g) in 10 ml of distilled water with pH of 7.0 adjusted using 1M HCl or NaOH.

The final composition of the sample in the reaction cell was therefore, 5 mg/ml of bile extract, 1.6 mg/ml of lipase, 5 mM $CaCl_2$).

Results

Figure 5:
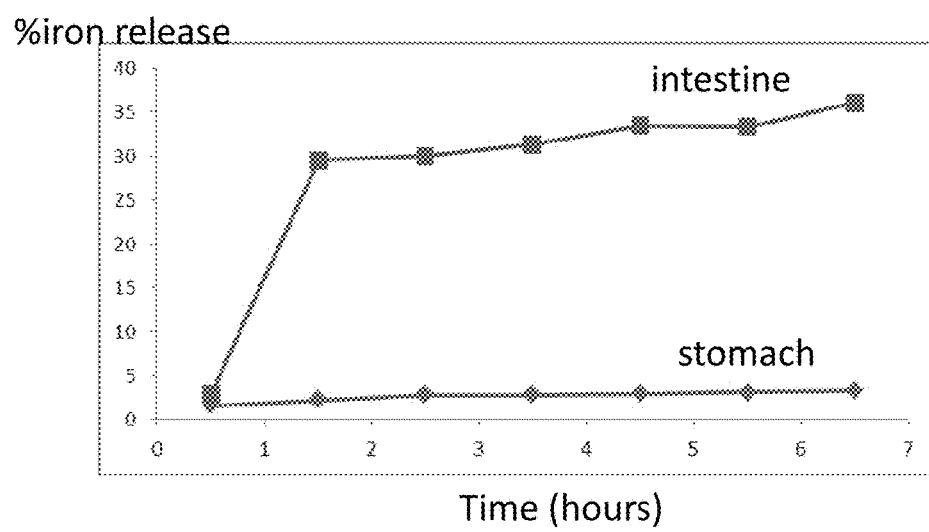
FIG. 5. Time course of iron release from iron oxide nanoparticle-containing bacteria in stomach and intestine mimic media. Note that the level of iron removed in intestine medium is significantly higher than that of stomach.

The samples (M1-M18) of *L. fermentum* specially prepared with maghemite were placed in appropriate vessels containing simulated stomach and intestine juices as appropriate and were incubated at 37° C. with continued stirring. Samples were taken at the following times: 0, 1, 2, 3, 4, 5 and 6 hours. Samples were centrifuged to decant bacteria and 900 µl of the supernatants were taken for analysis. Results show a small release of Fe under stomach conditions. The release is significantly higher under colon conditions and occurs mostly in the first hour (FIG. 5).

Figure 6:
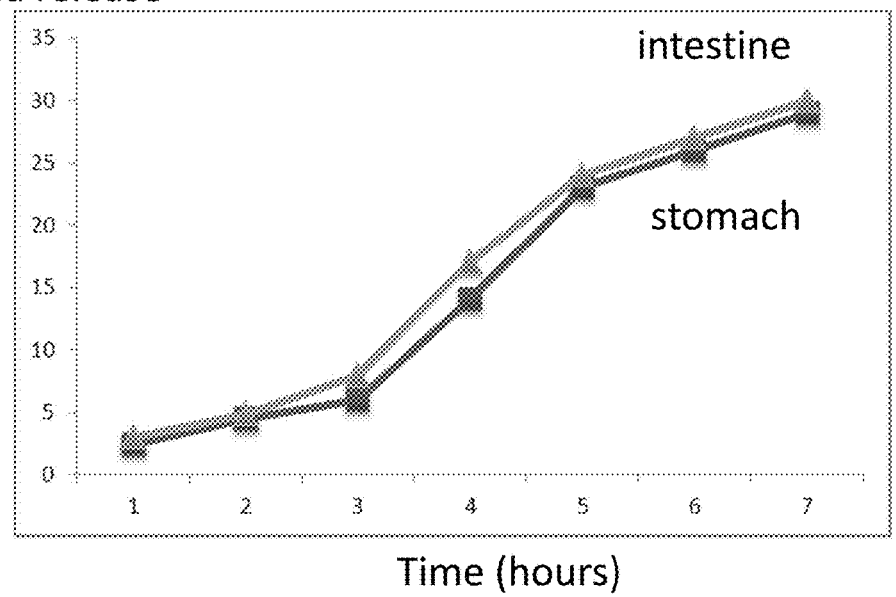
FIG. 6. Time course of calcium release by bacteria in stomach and intestine mimic media.
Figure 7:
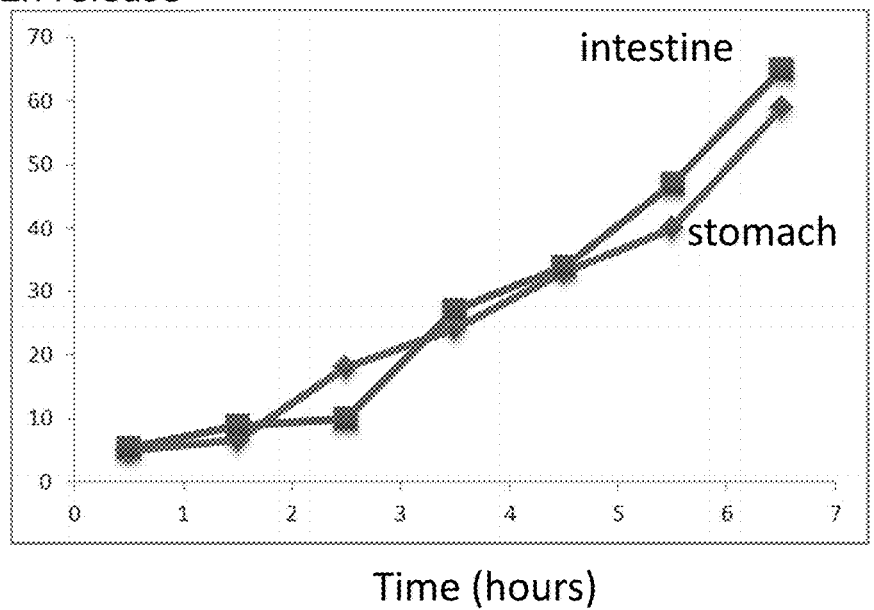
FIG. 7. Time course of zinc release by bacteria in stomach and intestine mimic media.

Following the same protocol, the metal release of calcium and zinc was analyzed in the presence and absence of magnetic nanoparticles (FIGS. 6 and 7).

Example 3

Metal Incorporation on the Bacterium Surface

Materials and Methods

Scanning electron microscopy (SEM) is one of the most powerful techniques for studying surface fine structures. SEM images were recorded by using a Zeiss SUPRA40VP Scanning Electron Microscope coupled with energy dispersive X-ray analyzer (EDX) X-Max 50 mm EDX is an analytical technique used for elemental analysis or chemical characterization. Samples were coated with carbon by arc discharge method for SEM-EDX.

Results

Figure 8:
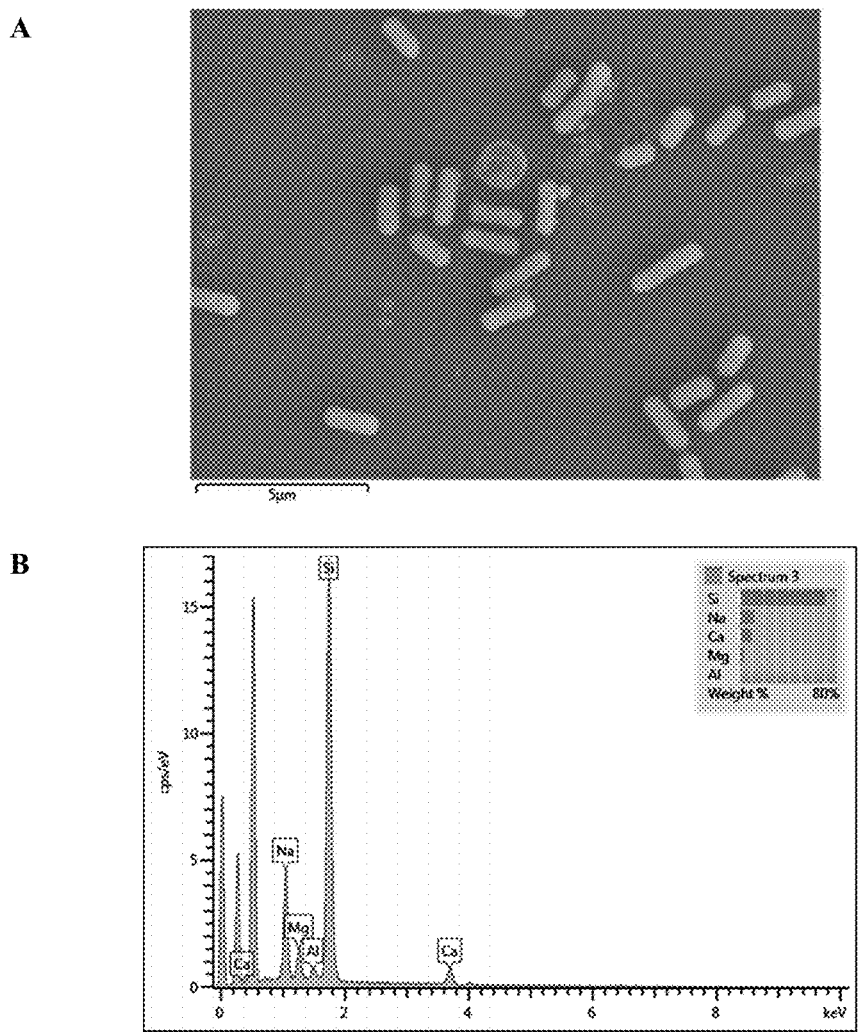
FIG. 8. (A) SEM image showing the bacteria after incubation with Ca2+. (B) EDX spectrum showed the Kα peak at 3.8 eV characteristic of Ca.

Energy dispersive x-ray spectroscopy was used to determine the elemental composition of the surface of individual bacteria. The SEM image of FIG. 8*a* shows the bacteria after incubation with $Ca^{2+}$. EDX spectrum showed the Kα peak at 3.8 eV characteristic of Ca, representing a value of around 10% in weight (FIG. 8*b*).

Figure 9:
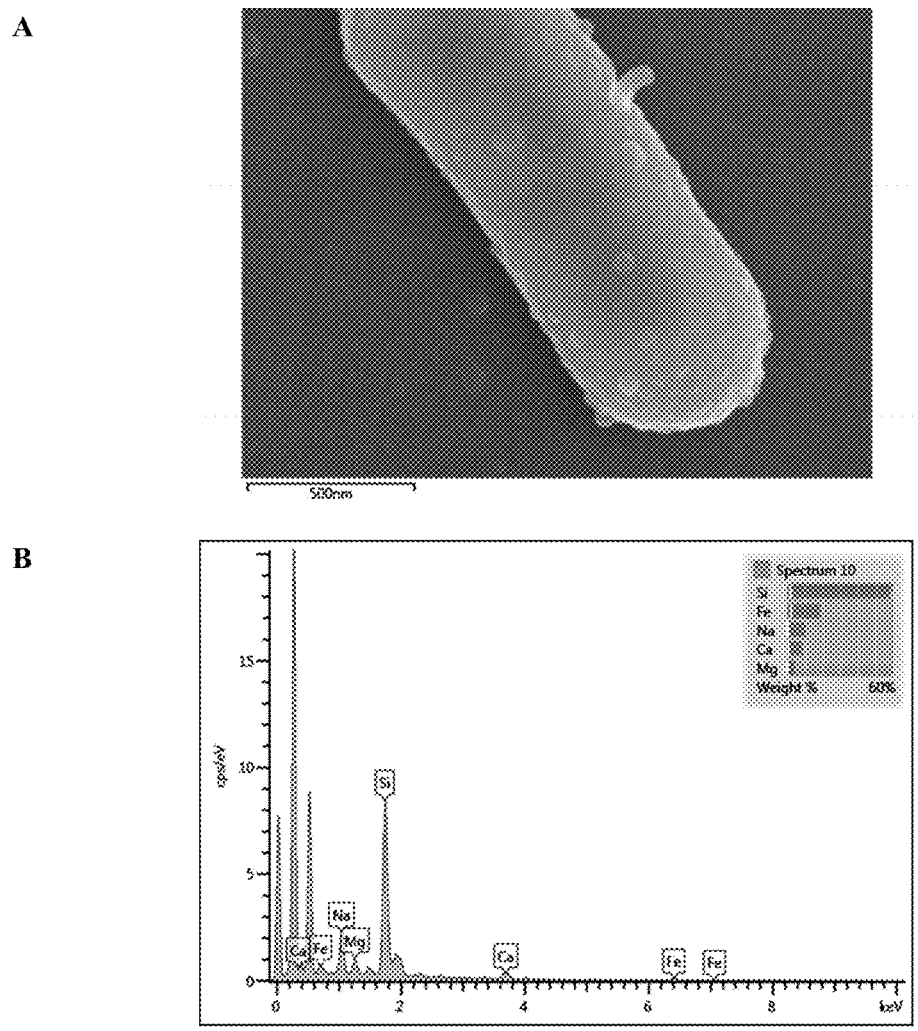
FIG. 9. (A) SEM image shows the bacteria after incubation with maghemite and Ca2+. (B) EDX spectrum showed the Kα peaks at 6.2 eV and 3.8 eV characteristic of Fe and Ca, respectively.

The SEM image of FIG. 9*a* shows the bacteria after incubation with maghemite and $Ca^{2+}$. EDX spectrum showed the Kα peaks at 6.2 eV and 3.8 eV characteristic of Fe and Ca, respectively (FIG. 9*b*). The iron represents a value of around 20% in weight while the percentage of calcium is 10%.

Example 4

Bacteria Containing Maghemite Nanoparticles as Oral MRI Contrast Agent

Materials and Methods

MRI measurements were performed with a 4.7T Biospec Tomograph System (Bruker, Karlsruhe, Germany) operating at 200 MHz and equipped with a 33 cm bore magnet (Oxford Ltd., UK).

In Vivo Experiments

In the in vivo experiments, normal Balb-c mice weighing about 20 g were used. Contrast agents were orally administered at different doses of Fe.

Results

MRI is one of the most powerful noninvasive modality for the diagnosis of many diseases in humans.

Figure 11:
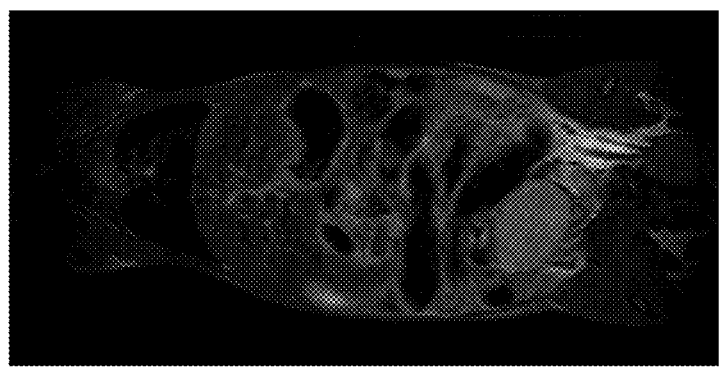
FIG. 11. A whole MRI body image of a mouse, after 12 h of administration of maghemite nanoparticles-containing bacteria. The morphology of some lower intestine parts is evident owing to the positive (dark) contrast due to the accumulation of magnetic nanoparticles.
Figure 10:
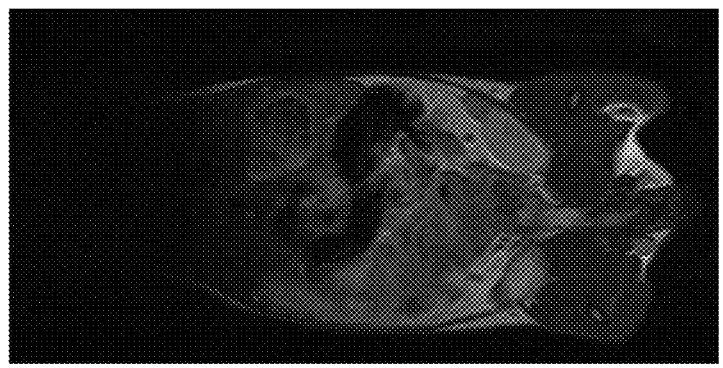
FIG. 10. A whole MRI body image of a mouse, after 6 h of administration of maghemite nanoparticles-containing bacteria. The morphology of some upper intestine parts is evident owing to the positive (dark) contrast due to the accumulation of magnetic nanoparticles.

The efficiency in contrasting MRI images of the bacteria once maghemite nanoparticles had been labeled was tested. The main advantages of the system are the following:

1. Bacteria serve as oral carriers of superparamagnetic maghemite nanoparticles.
2. Bacteria do not delivery maghemite nanoparticles at the stomach and therefore, MRI Images can be collected (FIG. 10). Control of the saturation level of particles onto bacteria or the amount of bacteria is necessary for an optima MRI acquisition.
3. Bacteria liberate the maghemite nanoparticles as pH rises and therefore a delivery of these particles take place during their trip along the intestines (FIG. 11).

The invention claimed is:

1. A bacterium selected from a lactic acid bacterium or a bacterium of the genus *Bifidobacterium*, the lactic acid bacterium and the bacterium of the genus *Bifidobacterium* comprising at least one metal nanoparticle directly bound to its surface through electrostatic interactions,
   wherein
   the metal nanoparticle is a magnetic nanoparticle
   or
   the metal nanoparticle is a nanoparticle wherein the metal within said metal nanoparticle is in the form of an oxide.

2. The bacterium according to claim 1 wherein the metal within the metal nanoparticle is selected from the group consisting of iron, manganese, cobalt, nickel, calcium, zinc, magnesium, potassium, copper, chromium, selenium, silicon, iodine and combinations thereof.

3. The bacterium according to claim 1 wherein the metal in the form of an oxide is iron oxide.

4. The bacterium according to claim 3 wherein the iron oxide is selected from the group consisting of maghemite, magnetite, hematite, goethite and ferrihydrite.

5. The bacterium according to claim 1 further comprising at least one additional metal different from the metal within said metal nanoparticle, wherein the at least one additional metal is comprised within the metal nanoparticle according to claim 1 or within a different and separate metal nanoparticle.

6. The bacterium according to claim 5 wherein the at least one additional metal is selected from the group consisting of iron, manganese, cobalt, nickel, calcium, zinc, magnesium, potassium, copper, chromium, selenium, silicon, iodine and combinations thereof.

7. The bacterium according to claim 1 further comprising at least one additional metal different from the metal within said metal nanoparticle, wherein the at least one additional metal is comprised within the metal nanoparticle according to claim 1 or within a different and separate metal nanoparticle,
   wherein the metal within the metal nanoparticle according to claim 1 is iron oxide and
   wherein the at least one additional metal is selected from the group consisting of iron, manganese, cobalt, nickel, calcium, zinc, magnesium, potassium, copper, chromium, selenium, silicon, iodine and a combination thereof.

8. The bacterium according to claim 1 wherein the nanoparticle has a size between 2 and 50 nm.

9. The bacterium according to claim 1 wherein the lactic acid bacterium is selected from the group consisting of *Lactobacillus fermentum, Lactobacillus gasseri, Lactobacillus reuteri, Lactobacillus coryniformis, Lactobacillus casei, Lactobacillus paracasei, Lactobacillus plantarum, Lactobacillus salivarius* and *Lactobacillus bulgaricus* and the bacterium of the genus *Bifidobacterium* is selected from the group consisting of *Bifidobacterium breve, Bifidobacterium longum, Bifidobacterium infantum* and *Bifidobacterium animalis*.

10. A method for obtaining a bacterium selected from a lactic acid bacterium or a bacterium of the genus *Bifidobacterium*, the lactic acid bacterium and the bacterium of the genus *Bifidobacterium* comprising at least one metal nanoparticle directly bound to its surface through electrostatic interactions, wherein the metal nanoparticle is a magnetic nanoparticle or the metal nanoparticle comprises a metal in the form of an oxide within said metal nanoparticle, the method comprising
contacting said bacterium with the at least one metal nanoparticle, wherein said contacting is carried out in the presence of at least one salt of a divalent cation and at a temperature wherein the growth of said bacterium is substantially reduced and at a pH in which said nanoparticle has a positive surface electrostatic charge.

11. A bacterium obtained by the method according to claim 10.

12. A biologically pure culture, foodstuff or a pharmaceutical composition comprising a bacterium according to claim 1, wherein the pharmaceutical composition further comprises a pharmaceutically acceptable carrier.

13. A therapeutic method for the treatment and/or prevention of a disease or condition associated with a metal deficiency, comprising administering to a subject a therapeutically effective amount of the bacterium of claim 1, wherein the bacterium comprises the metal that is deficient in said disease or condition and wherein the bacterium is administered orally.

14. A therapeutic method for the treatment and/or prevention of cancer, comprising administering to a subject a therapeutically effective amount of the bacterium of claim 1, wherein the metal is comprised in a magnetic nanoparticle.

15. A non-therapeutic method for the delivery of a metal into the intestine of a subject, comprising orally administering the bacterium according to claim 1.

16. A contrast agent comprising a bacterium according to claim 1 and a suitable carrier.

17. The contrast agent according to claim 16, wherein the magnetic nanoparticle comprises a metal within said magnetic nanoparticle.

18. A method for the magnetic resonance imaging of the digestive tract of a subject which comprises:
(i) orally administering to said subject the bacterium according to claim 1,
(ii) detecting the metal nanoparticles in the digestive tract of the subject.

19. The method according to claim 18 wherein the detection of the metal nanoparticles in the digestive tract of the subject is carried out between 1 and 5 hours after the oral administration thereby imaging the stomach or is carried out between 6 and 24 hours after the oral administration thereby imaging the intestine.

* * * * *